United States Patent
Bertrand et al.

(10) Patent No.: US 9,879,090 B2
(45) Date of Patent: Jan. 30, 2018

(54) FUSION PROTEINS AND IMMUNOCONJUGATES AND USES THEREOF WHICH ARE SPECIFIC FOR GLYCOPHORIN A

(71) Applicants: Institut National De La Santé Et De La Recherche Médicale (Inserm), Paris (FR); Université Paris Diderot - Paris 7, Paris (FR); Universite Des Antilles Et De La Guyane, Pointe-à-Pitre (FR); Institut National De La Transfusion Sanguine (INTS), Paris (FR)

(72) Inventors: Olivier Bertrand, Paris (FR); Ibrahim Habib, Le Kremlin-Bicêtre (FR); Dorota Smolarek, London (GB)

(73) Assignees: INSERM (Institut National De La SantéEt De La Recherche Médicale, Paris (FR); Imoversité Paris Diderot—Paris 7, Paris (FR); Universite Des Antilles Et De La Guyane, Pointe a Pitre (FR); Institut National De La Transfusion Sanguine (INTS), Paris (FR)

(*) Notice: Subject to any disclaimer, the term of this patent is extended or adjusted under 35 U.S.C. 154(b) by 326 days.

(21) Appl. No.: 14/772,339

(22) PCT Filed: Mar. 4, 2014

(86) PCT No.: PCT/EP2014/054161
§ 371 (c)(1),
(2) Date: Sep. 2, 2015

(87) PCT Pub. No.: WO2014/135528
PCT Pub. Date: Sep. 12, 2014

(65) Prior Publication Data
US 2016/0083481 A1 Mar. 24, 2016

(30) Foreign Application Priority Data
Mar. 4, 2013 (EP) .................................. 13305244

(51) Int. Cl.
*C07K 16/34* (2006.01)
*C07K 16/28* (2006.01)
*A61K 38/16* (2006.01)
*A61K 47/48* (2006.01)
*C07K 14/005* (2006.01)
*C12N 7/00* (2006.01)
*G01N 33/86* (2006.01)

(52) U.S. Cl.
CPC ............ *C07K 16/34* (2013.01); *A61K 38/162* (2013.01); *A61K 47/48246* (2013.01); *A61K 47/48561* (2013.01); *C07K 14/005* (2013.01); *C07K 16/2896* (2013.01); *C12N 7/00* (2013.01); *G01N 33/86* (2013.01); *C07K 2317/21* (2013.01); *C07K 2317/22* (2013.01); *C07K 2317/34* (2013.01); *C07K 2317/569* (2013.01); *C07K 2317/92* (2013.01); *C07K 2317/94* (2013.01); *C07K 2319/00* (2013.01); *C12N 2740/16022* (2013.01); *C12N 2740/16033* (2013.01); *G01N 2333/70596* (2013.01)

(58) Field of Classification Search
None
See application file for complete search history.

(56) References Cited

U.S. PATENT DOCUMENTS 5,086,002 A * 2/1992 Hillyard ............... G01N 33/531
422/535

FOREIGN PATENT DOCUMENTS

WO WO 2011/0147890 A1 12/2011

OTHER PUBLICATIONS

Czerwinski et al., N Biotechnol. Nov. 30, 2009;26(5):215-21. doi: 10.1016/j.nbt.2009.10.002. Epub Oct. 13, 2009.*
Atwell et al., Mol Immunol. Dec. 1996;33(17-18):1301-12.*
Wilson et al., J Immunol Methods. Oct. 14, 1994;175(2):267-73.*
Ghahroudi et al., FEBS Lett. Sep. 15, 1997;414(3):521-6.*
Barfield, C.A. et al., "A Highly Sensitive Rapid Diagnostic Test for Chagas Disease That Utilizes a Recombinant *Trypanosoma cruzi* Antigen" IEEE Trans Biomed Eng., Mar. 2011; pp. 814-817, vol. 58, No. 3.
Blumenfeld, O.O. et al., "Molecular genetics of glycophorin MNS variants" Transfus Clin Biol, 1997, pp. 357-365, vol. 4.
Branson, Bernard M. "Rapid Tests for HIV Antibody" AIDS Rev, 2000, pp. 76-83, vol. 2.
Branson, Bernard M. "Rapid HIV Testing: 2005 Update".
Carod, Jean-François et al., "Evaluation of the performance of 5 commercialized enzyme immunoassays for the detection of Taenia solium antibodies and for the diagnosis of neurocysticercosis" Diagnostic Microbiology and Infectious Disease, 2012, pp. 85-89, vol. 72.

(Continued)

*Primary Examiner* — Michael Szperka
(74) *Attorney, Agent, or Firm* — Knobbe Martens Olson & Bear LLP

(57) ABSTRACT

The present invention relates to isolated VHHs directed against human Glycophorin A. The present invention also relates to fusion proteins comprising the VHH according to the invention that is fused to at least one heterologous polypeptide and immunoconjugates comprising the VHH according to the invention that is conjugated to at least one chemical compound and their use in therapeutic or diagnostic methods.

19 Claims, 11 Drawing Sheets

(56) References Cited

OTHER PUBLICATIONS

Figure 1:
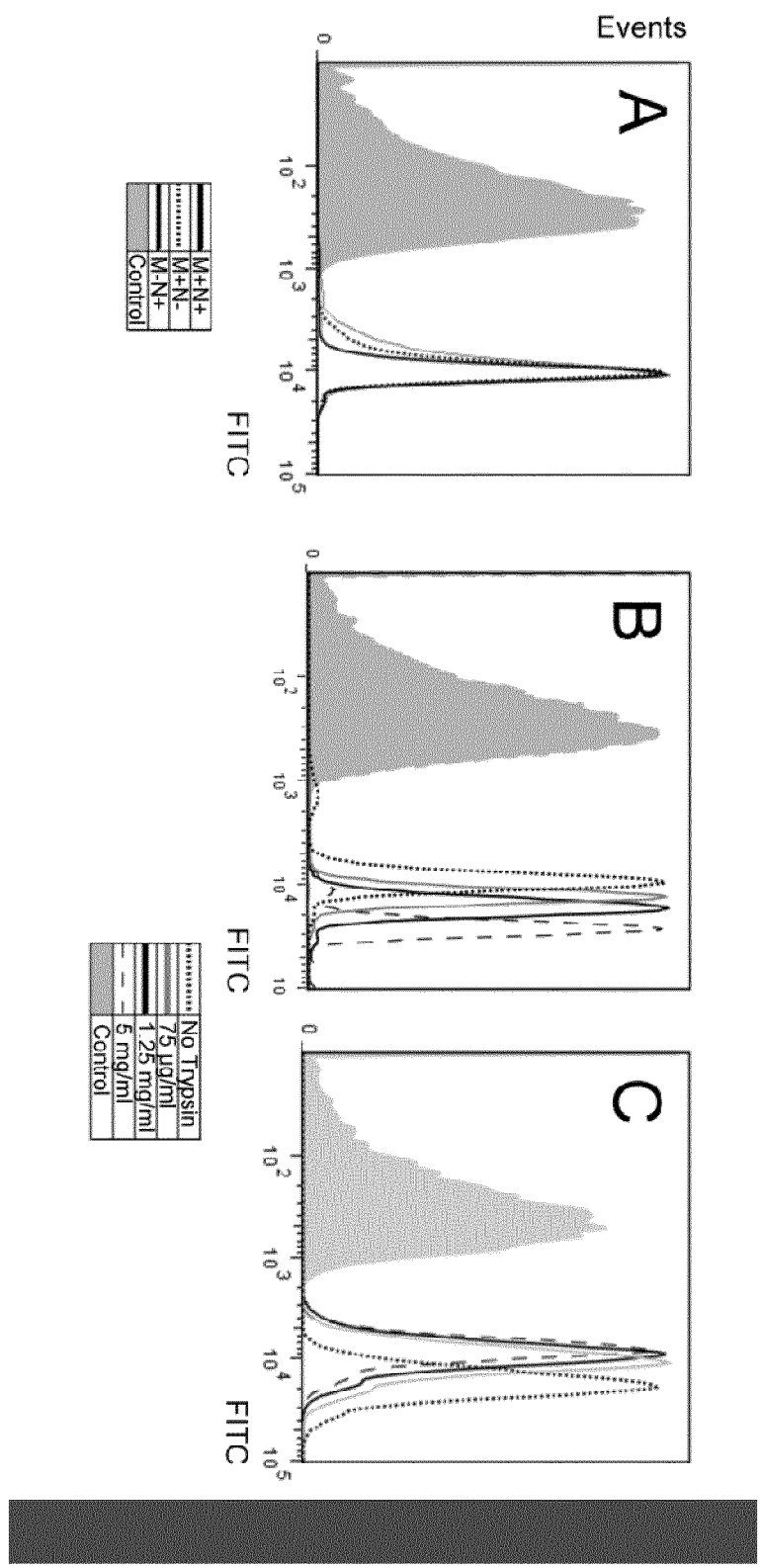

Cartron, J.P. et al., "MNSs and major glycophorins of human erythrocytes" TCB, 1995, pp. 251-258, vol. 4.

Chappuis, Francois et al., "Options for Field Diagnosis of Human African Trypanosomiasis" Clinical Microbiology Reviews, Jan. 2005, pp. 133-146, vol. 18, No. 1.

Chappuis, Francois et al., "A meta-analysis of the diagnostic performance of the direct agglutination test and rK39 dipstick for visceral leishmaniasis" BMJ, 2006, pp. 723-727, vol. 333.

Cochet, Sylvie et al., "New procedures for glycophorin A purification with high yield and high purity" Journal of Chromatography B, 2001, pp. 109-119, vol. 750.

Cohen, Myron S. et al., "Acute HIV-1 Infection" N Engl J Med., May 19, 2011; pp. 1943-1954, vol. 364, No. 20.

Daar, Eric S. et al., "Clinical presentation and diagnosis of primary HIV-1 infection" Current Opinion in HIV and AIDS, 2008, pp. 10-15, vol. 3.

De Genst, Erwin et al., "Molecular basis for the preferential cleft recognition by dromedary heavy-chain antibodies" PNAS, Mar. 21, 2006, pp. 4586-4591, vol. 103, No. 12.

Deschacht, Nick et al., "A Novel Promiscuous Class of Camelid Single-Domain Antibody Contributes to the Antigen-Binding Repertoire" Journal of Immunology, 2010, pp. 5696-5704, vol. 184.

Duk, Maria et al., "β-Elimination of O-Glycans from Glycoproteins Transferred to Immobilon P Membranes: Method and Some Applications" Analytical Biochemistry, 1997, pp. 98-102, vol. 253.

Ferreira, A.W. et al., "Enzyme-Linked Immunosorbent Assay for Serological Diagnosis of Chagas' Disease Employing a Trypanosoma cruzi Recombinant Antigen That Consists of Four Different Peptides" Journal of Clinical Microbiology, Dec. 2011, pp. 4390-4395, vol. 39, No. 12.

Geysen, H. Mario et al., "Strategies for epitope analysis using peptide synthesis" Journal of Immunological Methods, 1987, pp. 259-274, vol. 102.

Goto, Yasuyuki et al., "Cloning, Characterization, and Serodiagnostic Evaluation of Leishmania infantum Tandem Repeat Proteins" Infection and Immunity, Jul. 2006, pp. 3939-3945, vol. 74, No. 7.

Gupta, Amita et al., "Recombinant fusion proteins for haemagglutination-based rapid detection of antibodies to HIV in whole blood" Journal of Immunological Methods, 2001, pp. 121-140, vol. 256.

Gupta, Amita et al., "Expression, purification, and characterization of an anti-RBCFab-p24 fusion protein for hemagglutination-based rapid detection of antibodies to HIV in whole blood" Protein Expression and Purification, 2002, pp. 162-170, vol. 26.

Gupta, Amita et al., "Whole-Blood Agglutination Assay for On-Site Detection of Human Immunodeficiency Virus Infection" Journal of Clinical Microbiology, Jul. 2003, pp. 2814-2821, vol. 41, No. 7.

Habib, Ibrahim et al., "$V_HH$ (nanobody) directed against human glycophorin A: A tool for autologous red cell agglutination assays" Analytical Biochemistry, 2013, pp. 82-89, vol. 438.

Hassanzadeh-Ghassabeh, Gholamreza et al., "Generation of Anti-Infectome/Anti-proteome Nanobodies" Nanoproteomics: Methods and Protocols, Methods in Molecular Biology, 2011, pp. 239-259, vol. 790, Chapter 19.

Kemp, Bruce E. et al., "Autologous Red Cell Agglutination Assay for HIV-1 Antibodies: Simplified Test with Whole Blood" Science, 1988, pp. 1352-1354, vol. 241.

Lobstein, Julie et al., "SHuffle, a novel *Escherichia coli* protein expression strain capable of correctly folding disulfide bonded proteins in its cytoplasm" Microbial Cell Factories, 2012, pp. 1-16, vol. 11, No. 56.

Mabry, Robert et al., "Engineering of stable bispecific antibodies targeting IL-17A and IL-23" Protein Engineering, Design & Selection, 2010, pp. 115-127, vol. 23, No. 3.

McCarthy, James S. et al., "A Research Agenda for Helminth Diseases of Humans: Diagnostics for Control and Elimination Programmes" PLOS Neglected Tropical Diseases, Apr. 2012, pp. 1-13, vol. 6, Issue 4, e1601.

Misselwitz, Rolf et al., "Conformation and stability of recombinant HIV-1 capsid protein p24 (rp24)" Biochimica et Biophysica Acta, 1995, p. 9-18, vol. 1250.

Mohamad, Suharni et al., "Development and Evaluation of a Sensitive and Specific Assay for Diagnosis of Human Toxocariasis by Use of Three Recombinant Antigens (TES-26, TES-30USM, and TES-120)" Journal of Clinical Microbiology, Jun. 2009, pp. 1712-1717, vol. 47, No. 6.

Murphy, G. et al., "Assays for the detection of recent infections with human immunodeficiency virus type 1" Eurosurveillance, Jul.-Sep. 2008, pp. 4-10, vol. 13, Issues 7-9.

Muyldermans, Serge et al., "Single domain camel antibodies: current status" Reviews in Molecular Biotechnology, 2001, pp. 277-302, vol. 74.

Nguyen, Viet Khong et al., "Camel heavy-chain antibodies: diverse germline $V_HH$ and specific mechanisms enlarge the antigen-binding repertoire" The EMBO Journal, 2000, pp. 921-930, vol. 19, No. 5.

Nieuwenhove, Liesbeth Van et al., "Identification of Mimotopes with Diagnostic Potential for Trypanosoma brucei gambiense Variant Surface Glycoproteins Using Human Antibody Fractions" PLoS One, Jun. 2012, pp. 1-11, vol. 6, Issue 6, e1682.

Rahuel, Cécile et al., "Characterization of cDNA clones for human glycophorin A Use for gene localization and for analysis of normal of glycophorin-A-deficient (Finnish type) genomic DNA" Eur. J. Biochem., 1988, pp. 147-153, vol. 172.

Rahuel, Cécile et al., "Alteration of the genes for glycophorin A and B in glycophorin-A-deficient individuals" Eur. J. Biochem., 1988, pp. 605-614, vol. 177.

Reid, M.E. et al., "Coordinator's Report: Glycophorin/Band 3 and associated antigens" TCB, 1997, pp. 57-64, vol. 1.

Rylatt, Dennis B. et al., "A rapid whole-blood immunoassay system" the Medical Journal of Australia, Jan. 15, 1990, pp. 75-77, vol. 152.

Sirivichayakul, Sunee et al., "Evaluation of a 2-Minute Anti-Human Immunodeficiency Virus (HIV) Test Using the Autologous Erythrocyte Agglutination Technique with Populations Differing in HIV Prevalence" Journal of Clinical Microbiology, May 1993, pp. 1373-1375, vol. 31, No. 5.

Smolarek, Dorota et al., "A recombinant dromedary antibody fragment (VHH or nanobody) directed against human Duffy antigen receptor for chemokines" Cellular and Molecular Life Sciences, 2010, pp. 3371-3387, vol. 67.

Srivastava, Anand et al., "Var2CSA Minimal CSA Binding Region Is Located within the N-Terminal Region" PLoS One, May 2011, pp. 1-10, vol. 6, Issue 5, e20270.

Veggiani, Gianluca et al., "Improved quantitative and qualitative production of single-domain intrabodies mediated by the co-expression of Erv1p sulfhydryl oxidase" Protein Expression and Purification, 2011, pp. 111-114, vol. 79.

Vincke, Cécile et al., "General Strategy to Humanize a Camelid Single-domain Antibody and Identification of a Universal Humanized Nanobody Scaffold" The Journal of Biological Chemistry, Jan. 30, 2009, pp. 3273-3284, vol. 284, No. 5.

Vincke, Cécile et al., "Generation of single domain antibody fragments derived from camelids and generation of manifold constructs" Methods in Molecular Biology, 2012, pp. 145-176, vol. 907.

Wasniowska, K. et al., "Mapping of peptidic epitopes of glycophorins A (GPA) and C (GPC) with peptides synthesized on plastic pins (Pepscan analysis)" TCB, 1997, pp. 73-75, vol. 1.

Wesolowski, Janusz et al., "Single domain antibodies: promising experimental and therapeutic tools in infection and immunity" Med Microbiol Immunol, 2009, pp. 157-174, vol. 198.

White, A. Clinton "Neurocysticercosis: A Major Cause of Neurological Disease Worldwide" CID, Feb. 1997, pp. 101-115, vol. 24.

International Search Report for PCT/EP2014/054161 dated Jun. 5, 2014.

\* cited by examiner

IH51 100μg/mL     50 μg/mL     2.5μg/mL     0.5 μg/mL

IH51 2.5 μg/mL         IH4 2.5 μg/mL
+ p24 50μg/mL

IH51 2.5 μg/mL
control plasma

Figure 11

FUSION PROTEINS AND IMMUNOCONJUGATES AND USES THEREOF WHICH ARE SPECIFIC FOR GLYCOPHORIN A

CROSS REFERENCE TO RELATED APPLICATIONS

This application is a U.S. National Phase Application of PCT International Application Number PCT/EP2014/054161, filed on Mar. 4, 2014, designating the United States of America and published in the English language, which is an International Application of and claims the benefit of priority to European Patent Application No. 13305244.9, filed on Mar. 4, 2013. The disclosures of the above-referenced applications are hereby expressly incorporated by reference in their entireties.

FIELD OF THE INVENTION

The present invention relates to VHHs directed against human Glycophorin and derivatives thereof which can be used in therapy and for diagnostic assays.

BACKGROUND OF THE INVENTION

VHHs, also known as single domain antibodies (sdAbs) or Nanobodies™, are variable domains derived from heavy chain antibodies present in camelids. Recombinant VHHs are obtained by screening libraries prepared from lymphocyte RNA of naïve or immunized animals, they are renowned for their easy cloning and expression, and have many applications in research, therapy and diagnosis (1-3).

Aiming to obtain VHH directed against various antigens present on human red blood cells, the inventors immunized a dromedary by transfusion of human blood and derived a VHH library from the animal's lymphocytes. Since VHH that recognizes indiscriminately red cells of all humans may have interesting applications the inventors screened the library against glycophorin A (GPA) a protein present at a high copy number on red cells and isolated several VHHs: One of them which represented 67% of all isolated sequences was fully characterized and is described.

Glycophorins A (GPA) and B (GPB) are essentially expressed on red cells (even though some expression was detected in renal tissue). Expression level is as high as 800 000 copies per cell for GPA and 200 000 copies for GPB (4-5). The highly homologous GPA and GPB are encoded by two genes derived one from the other after a gene duplication event. The sequence of the 26 N-terminal amino acids of GPB is identical to one of the two alloforms of GPA N-terminus. GPA and GPB are single transmembrane domain proteins with a heavily glycosylated extracellular domain. GPA and GPB do associate in the red cell membrane hence homodimers and heterodimers of GPA and GPB are present in the membrane as shown by SDS polyacrylamide gel electrophoresis of red cells membrane extracts. Glycophorins carry several blood group antigens, the most important of them are M and N blood group antigens on GPA, N, S and s antigens on GPB. Blood group antigens carried by glycophorins are important for transfusion medicine and may be responsible for adverse reactions in case of poorly matched transfusion and also be responsible of hemolytic disease of the newborn. Moreover glycophorins carry antigens which are independent of blood groups and several murine monoclonal antibodies exist that target such epitopes constantly present on the molecules independently of the blood group (6).

The present invention demonstrates that the isolated VHH may be used for autologous red cells agglutination assays (7-9). In short monovalent VHH fused to an antigen added to whole blood taken from a patient may induce red cells agglutination if patient's plasma contains antibodies directed against fused antigen.

Many drugs have limited therapeutic action because they are rapidly eliminated from the body when administered. For example, many polypeptides, peptides or chemical compounds that have therapeutically useful activities are rapidly cleared from the circulation via the kidney. Accordingly, a large dose must be administered in order to achieve a desired therapeutic effect. Accordingly, there is a need of developing fusion proteins or immunoconjugates which because of their properties to interact with red cells may increase drug serum half-life.

SUMMARY OF THE INVENTION

The present invention relates to isolated VHHs directed against human Glycophorin A.

The present invention also relates to fusion proteins comprising the VHH according to the invention that is fused to at least one heterologous polypeptide and immunoconjugates comprising the VHH according to the invention that is conjugated to at least one chemical compound and their use in therapeutic methods or diagnostic assays.

DETAILED DESCRIPTION OF THE INVENTION

The present invention describes the preparation of a VHH (Nanobody™) named IH4 and related VHH with similar amino-acid sequence (called collectively IH4like) that recognize human glycophorin A (GPA). IH4 and IH4like were isolated by screening a library prepared from the lymphocytes of a dromedary immunized by transfusion of human blood. Phage display and panning against GPA as immobilized antigen, allowed isolating this VHH. IH4 represented 67% of the retrieved $V_H H$ sequences. IH4 was expressed as a soluble correctly folded protein in SHuffle™ E. coli cells yielding routinely ca. 100 mg/L fermentation medium. IH4 and IH4like recognize GPA independently of the blood group antigen; hence they recognize red cells of all humans with the possible exception of those with some extremely rare genetic background. The targeted linear epitope comprises the $Y_{52}PPE_{55}$ sequence. Dissociation constant of the IH4-GPA equilibrium is 33 nM as computed from Surface Plasmon Resonance (SPR) results. IH4 is a stable protein with a transition melting temperature of 75.8° C. (measured by Differential Scanning Calorimetry, DSC). As a proof of concept, the inventors fused HIV p24 to IH4 and used the purified construct expressed in E. coli to show that IH4 was amenable to the preparation of autologous erythrocytes agglutination reagents: reconstituted blood prepared with serum from a HIV positive patient was readily agglutinated by addition of the bifunctional reagent.

VHHs of the Invention

The present invention provides isolated VHHs recognizing Human Glycophorin A (GPA).

The term "VHH" or "single domain antibody" (sdAb) refers to the single heavy chain variable domain of antibodies of the type that can be found in Camelids which are naturally devoid of light chains. Such VHH are also called "Nanobody®". The term "VHH" refers to the single heavy chain having 3 complementarity determining regions (CDRs): CDR1, CDR2 and CDR3. The term "complementarity determining region" or "CDR" refers to the hypervariable amino acid sequences which define the binding affinity and specificity of the VHH.

The term "Human Glycophorin A" or "GPA" refers to a protein essentially expressed on red blood cells (even though some expression was detected in renal tissue). Human Glycophorin A, also known as GYPA, is a protein which is encoded by the GYPA gene (CD235a) and refers to a single transmembrane domain proteins with a heavily glycosylated extracellular domain.

In particular, the isolated VHHs according to the invention recognized the particular epitope YPPE sequence set forth as SEQ ID NO:17.

In particular the present invention relates to an isolated VHH comprising a CDR1 having at least 70%, or at least 80%, or at least 90% of identity with sequence set forth as SEQ ID NO: 1, a CDR2 having at least 70%, or at least 80%, or at least 90% of identity with sequence set forth as SEQ ID NO:2 and a CDR3 having at least 70%, or at least 80%, or at least 90% of identity with sequence set forth as SEQ ID NO:3.

Amino acid sequence identity is preferably determined using a suitable sequence alignment algorithm and default parameters, such as BLAST P (Karlin and Altschul, Proc. Natl Acad. Sci. USA 87(6):2264-2268 (1990)).

In some embodiment the isolated VHH according to the invention comprises a CDR1 having a sequence set forth as SEQ ID NO: 1, a CDR2 having a sequence set forth as SEQ ID NO:2 and a CDR3 having a sequence set forth as SEQ ID NO:3

In some embodiment the isolated VHH according to the invention comprises a CDR1 having a sequence set forth as SEQ ID NO:4, a CDR2 having a sequence set forth as SEQ ID NO:5 and a CDR3 having a sequence set forth as SEQ ID NO:6.

In a particular embodiment, the isolated VHH according to the invention is a humanized VHH.

By "humanized", it is meant mutated so that immunogenicity upon administration in human patients is minor or nonexistent. Humanizing a VHH according to the present invention, comprises a step of replacing one or more of the amino acids of said VHH by their human counterpart as found in the human consensus sequence, without that VHH losing its typical character, i. e. the humanization does not significantly affect the antigen binding capacity of the resulting VHH.

In some embodiments, the isolated VHH comprises an amino acid sequence that has at least about 80%, or at least about 85%, or at least about 90%, or at least about 95%, or at least about 96%, or at least about 97%, or at least about 98%, or at least about 99% amino acid sequence identity with a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

In a particular embodiment, the isolated VHH according to the invention has an amino acid sequence selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

Fusion Proteins of the Invention

A further aspect of the present invention relates to a fusion protein comprising a VHH according to the invention that is fused to at least one heterologous polypeptide.

The term "fusion protein" refers to the VHH directed against human glycophorin A (GPA) that is fused directly or via a spacer to at least one heterologous polypeptide.

According to the invention, the fusion protein comprises the VHH according to the invention that is fused either directly or via a spacer at its C-terminal end to the N-terminal end of the heterologous polypeptide, or at its N-terminal end to the C-terminal end of the heterologous polypeptide.

As used herein, the term "directly" means that the (first or last) amino acid at the terminal end (N or C-terminal end) of the VHH is fused to the (first or last) amino acid at the terminal end (N or C-terminal end) of the heterologous polypeptide.

In other words, in this embodiment, the last amino acid of the C-terminal end of said VHH is directly linked by a covalent bond to the first amino acid of the N-terminal end of said heterologous polypeptide, or the first amino acid of the N-terminal end of said VHH is directly linked by a covalent bond to the last amino acid of the C-terminal end of said heterologous polypeptide.

As used herein, the term "spacer" refers to a sequence of at least one amino acid that links the VHH of the invention to the heterologous polypeptide. Such a spacer may be useful to prevent steric hindrances.

In some embodiments, the heterologous polypeptide is an antigen.

In a particular embodiment, the antigen may be selected from infectious antigens. As used herein, the term "infectious antigens" refers to an antigen derived from infectious agents and that is capable of being bound by an antibody.

In a particular embodiment, the antigen is a HIV p24 antigen.

In another embodiment, the heterologous polypeptide is an antibody.

In another embodiment, the heterologous polypeptide is a VHH.

In a particular embodiment, the antibody or the VHH may be directed against an infectious agent.

The term "infectious agent" is intended to encompass any virus, bacteria or parasite pathogens. Therefore the term includes but is not limited to virus such as human immunodeficiency virus, Hepatitis B virus, hepatitis C virus, parasites such as *Plasmodium Falciparum* (causative agent for Malaria), the agents of African and American Trypanosomiasis, of Leishmaniosis, the agents of various helminthiasis like onchocerciasis, filariasis, threadworm infections shistosomiasis cysticercosis (McCarthy J S, Lustigman S, Yang G J, Barakat R M, Garcia H H, Sripa B, Willingham A L, Prichard R K, Basáñez M G. A research agenda for helminth diseases of humans:diagnostics for control and elimination programmes. PLoS Negl Trop Dis. 2012; 6(4): e1601. doi: 10.1371/journal.pntd.0001601.), Toxocariosis or bacteria such as *mycobacterium tuberculosis, mycobacterium leprae* or the agent of Buruli ulcer.

In a particular embodiment, the antibody or the VHH is a therapeutic antibody. The therapeutic antibodies include but are not limited to Abciximab, Adalimumab, Alemtuzumab, Basiliximab, Belimumab, Bevacizumab (Avastin), entuximab vedotin, Canakinumab, Cetuximab, Certolizumab pegol, Daclizumab, Denosumab, Eculizumab, Efalizumab, Gemtuzumab, Golimumab, Ibritumomab tiuxetan, Infliximab, Ipilimumab (MDX-101), Muromonab-CD3, Natalizumab, Ofatumumab, Omalizumab, Palivizumab, Panitumumab, Ranibizumab, Rituximab, Tocilizumab (or Atlizumab), Tositumomab, and Trastuzumab (Herceptin).

In another embodiment, the heterologous polypeptide is a therapeutic polypeptide.

The term "therapeutic polypeptide" refers to any polypeptide that can be administered to a patient to produce a beneficial therapeutic or diagnostic effect though binding to and/or altering the function of a biological target molecule in the patient. The target molecule can be an endogenous target molecule encoded by the patient's genome (e.g., an enzyme, receptor, growth factor, cytokine encoded by the patient's genome) or an exogenous target molecule encoded by the genome of a pathogen (e.g., an enzyme encoded by the genome of a virus, bacterium, fungus, nematode or other pathogen).

Typically, therapeutic polypeptides include but are not limited to polypeptide toxin, for example, a toxin such as abrin, ricin A, *pseudomonas* exotoxin, or diphtheria toxin. Other suitable therapeutic polypeptides include antibodies or antigen-binding fragments (e.g., dAbs) of antibodies, polypeptide agonists, activators, secretagogues, antagonists or inhibitors.

In one embodiment, the therapeutic polypeptides of the invention can be an agonist or an antagonist of a cell surface protein, such as a CD antigen, cytokine receptor (e.g., interleukin receptor, chemokine receptor), adhesion molecule or costimulatory molecule. For example, the therapeutic polypeptide can bind a cytokine, growth factors, cytokine receptor, growth factor receptor and other target ligand, which include but are not limited to: ApoE, Apo-SAA, BDNF, Cardiotrophin-1, CEA, CD40, CD40 Ligand, CD56, CD38, CD138, EGF, EGF receptor, ENA-78, Eotaxin, Eotaxin-2, Exodus-2, FAPα, FGF-acidic, FGF-basic, fibroblast growth factor-10, FLT3 ligand, Fractalkine (CX3C), GDNF, G-CSF, GM-CSF, GF-β1, human serum albumin, insulin, IFN-γ, IGF-I, IGF-II, IL-1α, IL-1β, IL-1 receptor, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, OncostatinM, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF A, VEGF B, VEGF C, VEGF D, VEGF receptor 1, VEGF receptor 2, VEGF receptor 3, GCP-2, GRO/MGSA, GRO-β, GRO-γ, HCC1, 1-309, HER 1, HER 2, HER 3 and HER 4.

Therapeutic polypeptides of the invention also include hormones, including pituitary hormone (PTH), adrenocorticotropic hormone (ACTH), renin, luteinizing hormone-releasing hormone (LHRH), gonadotropin-releasing hormone (GnRH), luteinizing hormone (LH), follicle stimulating hormone (FSH), aldosterone, and the like. Suitable therapeutic polypeptides also include keratinocyte growth factor, interferons (e.g., IFN-α, IFN-β, IFN-γ), erythropoietin (EPO), proteases, elastases, LHRH analogs, agonists and antagonists, opioid receptor agonists, such as kappa opioid receptor agonists (e.g., dynorphin A), calcitonin and calcitonin analogs, antidiuretic hormone (vasopressin), oxytocin antagonists, vasoactive intestinal peptide, thrombin inhibitors, von Willebrand factor, surfactants and snail venom (e. g., ziconotide).

Therapeutic polypeptides of the invention also include peptides and polypeptides that have anti-cancer activities (e.g., proliferation inhibiting, growth inhibiting, apoptosis inducing, metastasis inhibiting, adhesion inhibiting, neovascularization inhibiting). Several such peptides and polypeptides are known in the art. (See. e.g., Janin Y. L., Amino Acids, 25: 1-40 (2003). The entire teaching of this reference, particularly the peptides and polypeptides disclosed therein, are incorporated herein by reference.

The therapeutic polypeptides can also be a cytokine or growth factor or soluble portion of a receptor (e.g., a cytokine receptor, growth factor receptor, hormone receptor) or other polypeptide such as the polypeptides listed above. For example, suitable therapeutic polypeptides also include receptor (e.g., growth factor receptor, cytokine receptor, hormone receptor) agonists and antagonists, such as interleukin 1 receptor antagonist (Eisenberg et al., Nature 343: 341-346 (1990)), thrombopoietin receptor agonists (e.g., GW395058 (de Serres et al., Stem Cells 17: 316-326 (1999)), melanocortin receptor antagonists (e.g., MCR-4 antagonists (Cepoi et al., Brain Res. 1000:64-71 (2004)), anginex, 6DBF7 (Mayo et al., J. Biol. Chem. 278:45746-45752 (2003)), chemokine mimetics (e.g., RANTES mimetics (Nardese et al., Nat. Struct. Biol. 8: 611-615 (2001)), growth hormone (e. g., human growth hormone), growth hormone analogs and growth hormone secretagogues (e.g., CP-424,391 (MacAndrew et al., Eur. J. Pharmacol. 432: 195-202 (2001)), growth hormone releasing hormone mimetics (e.g., MK-677 (Chapman et al., J. Clin. Endocrinol. Metab. 82: 3455-3463 (1997)), inhibitors of cellular adhesion molecule interactions (e.g., LFA-1/ICAM-1, VLA-1/VCAM-1 (Yusuf-Makagiansar et al., Med. Res. Rev. 22: 146-167 (2002)), mimetics of interferon (e.g., SYR6 (Sato et al., Biochem. J. 371(Pt.2):603-608 (2003), mimetics of herceptin (Nature Biotechnol. 18: 137 (2000)), inhibitors of antigen presentation (Bolin et al., J: Med. Chem. 43:2135-2148 (2000)), GPIIB/IIIA antagonists (e.g., FK633 (Aoki et al., Thromb. Res. 81:439-450 (1996)), alphavbeta3 antagonists (e.g., SC56631 (Engleman et al., J. Clin. Invest. 99: 2284-2292 (1997)), erythropoietin mimetics (e.g., EMP1 (Johnson et al., Biochemistry 37: 3699-3710 (1998)), opioid receptor antagonists (e.g., [(2S,3R)-TMTI]DPDPE (Liao et al., J. Med. Cheni. 41: 4767-4776 (1998)), hematopoietic factors (e.g., erythropoietin (EPO), granulocyte colony stimulating factor (GM-CSF)).

Additional suitable therapeutic polypeptides include peptide antagonists that bind human type 1 IL-1 receptor (e.g., AF11377), AF11869 (J=1-azetidine-2-carboxylic acid), or any of the foregoing sequences optionally containing an acylated amino terminus and/or an aminated carboxyl terminus (Akeson et al., J. Biol. Chem. 271: 30517-305123 (1996)), peptide antagonists of TNF-alpha-mediated cytotoxicity (e. g., those disclosed in Chirinos-Rojas et al, J. Immunol. 161: 5621-5626 (1998)), peptide agonists of erythropoietin receptor (e. g., those disclosed in McConnel et al., Biol. Chem. 379: 1279-1286 (1998) or Wrighton et al., Science 273: 458-464 (1996)), glucagon-like peptide-1 (GLP-1. e.g. GLP-1 (7-37), GLP-1 (7-36)amide and analogs thereof (see, e.g., Ritzel U. et al., J. Endocrinology 159:93-102 (1998)), and interferons (e.g., INFα, INFβ, INFγ). Additional suitable therapeutic polypeptides include integrin inhibitors (e.g., RGD peptides (Janssen, M. L., et al., Cancer Research 62: 6146-6151 (2002); (Kantlehner M., et al., Agnew. Chem. Int. Ed. 38: 560 (1999); (Haubner, R., et al., J Nucl. Med. 42: 326-336 (2001)), ribosome-inactivating proteins (RIPs) such as Saporin, matrix metalloproteinase inhibitors (e.g., U.S. Pat. No. 5,616,605), and antiviral peptides and polypeptides, such as HIV fusion inhibitors (e.g., T-1249 and T-20 (FUZEON® (enfuvirtide); Trimeris Inc.), and soluble receptor antagonists such as immunoadhesins (e.g., LFA3-Ig, CTLA4-Ig).

In one embodiment, the therapeutic polypeptides of the invention is selected from antimicrobial polypeptide and peptide drugs such as adenoregulin, dermcidin-1L, cathelicidins (e.g., cathelicidin-like peptide, human LL-37/hCAP-18), defensins, including a-defensins (e.g., human neutrophil peptide 1 (HNP-1), HNP-2, HNP-3, HNP-4, human defensin 5, human defensin 6), β-defensins (e.g., human β-defensin-1, human β-defensin-2), and O-defensins (e.g., θ-defensin-1), histatins (e.g., histatin 1, histatin 3, histatin 5), lactoferricin-derived peptide and related peptides (see, Tomita M., et al., Acta Paediatr. Jpn. 36: 585-591 (1994) and Strom, M. B., et al. Biochem Cell Biol. 80: 65-74 (2002)).

VHH and Fusion Proteins Production Methods

The VHH and fusion protein according to the invention can readily be prepared by an ordinarily skilled artisan using routine experimentation. The VHH variants and modified form thereof may be produced under any known technique in the art such as in-vitro maturation.

VHHs or sdAbs are usually generated by PCR cloning of the V-domain repertoire from blood, lymph node, or spleen cDNA obtained from immunized animals into a phage display vector, such as pHEN2. Antigen-specific VHHs are commonly selected by panning phage libraries on immobilized antigen, e.g., antigen coated onto the plastic surface of a test tube, biotinylated antigens immobilized on streptavidin beads, or membrane proteins expressed on the surface of cells. However, such VHHs often show lower affinities for their antigen than VHHs derived from animals that have received several immunizations. The high affinity of VHHs from immune libraries is attributed to the natural selection of variant VHHs during clonal expansion of B-cells in the lymphoid organs of immunized animals. The affinity of VHHs from non-immune libraries can often be improved by mimicking this strategy in vitro, i.e., by site directed mutagenesis of the CDR regions and further rounds of panning on immobilized antigen under conditions of increased stringency (higher temperature, high or low salt concentration, high or low pH, and low antigen concentrations). VHHs derived from camelid are readily expressed in and purified from the *E. coli* periplasm at much higher levels than the corresponding domains of conventional antibodies. VHHs generally display high solubility and stability and can also be readily produced in yeast, plant, and mammalian cells. For example, the "Hamers patents" describe methods and techniques for generating VHH against any desired target (see for example U.S. Pat. No. 5,800,988; U.S. Pat. No. 5,874,541 and U.S. Pat. No. 6,015,695). The "Hamers patents" more particularly describe production of VHHs in bacterial hosts such as *E. coli* (see for example U.S. Pat. No. 6,765,087) and in lower eukaryotic hosts such as moulds (for example *Aspergillus* or *Trichoderma*) or in yeast (for example *Saccharomyces, Kluyveromyces, Hansenula* or *Pichia*) (see for example U.S. Pat. No. 6,838,254).

Nucleic Acids, Vectors and Recombinant Host Cells of the Invention

A further object of the present invention relates to a nucleic acid molecule encoding for a VHH or a fusion protein according to the invention.

As used herein, a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

These nucleic acid molecules can be obtained by conventional methods well known to those skilled in the art.

Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule encoding for a VHH or a fusion protein of the invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Any expression vector for animal cell can be used. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vectors include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

A subject of the present invention is also a prokaryotic or eukaryotic host cell genetically transformed with at least one nucleic acid molecule or vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

In a particular embodiment, for expressing and producing VHHs or fusion proteins of the invention, prokaryotic cells, in particular *E. coli* cells, will be chosen. Actually, according to the invention, it is not mandatory to produce the VHH or the fusion protein of the invention in a eukaryotic context that will favour post-translational modifications (e.g. glycosylation). Furthermore, prokaryotic cells have the advantages to produce protein in large amounts. If a eukaryotic context is needed, yeasts (e.g. *saccharomyces* strains) may be particularly suitable since they allow production of large amounts of proteins. Otherwise, typical eukaryotic cell lines such as CHO, BHK-21, COS-7, C127, PER.C6, YB2/0 or HEK293 could be used, for their ability to process to the right post-translational modifications of the fusion protein of the invention.

Accordingly, a further aspect of the invention relates to a host cell comprising a nucleic acid molecule encoding for a VHH or a fusion protein according to the invention or a vector according to the invention.

The construction of expression vectors in accordance with the invention, and the transformation of the host cells can be carried out using conventional molecular biology techniques. The VHH or the fusion protein of the invention, can, for example, be obtained by culturing genetically transformed cells in accordance with the invention and recovering the VHH or the fusion protein expressed by said cell, from the culture. They may then, if necessary, be purified by conventional procedures, known in themselves to those skilled in the art, for example by fractional precipitation, in particular ammonium sulfate precipitation, electrophoresis, gel filtration, affinity chromatography, etc. In particular, conventional methods for preparing and purifying recombinant proteins may be used for producing the proteins in accordance with the invention.

A further aspect of the invention relates to a method for producing a VHH or a fusion protein of the invention comprising the step consisting of: (i) culturing a transformed host cell according to the invention under conditions suitable to allow expression of said VHH or fusion protein; and (ii) recovering the expressed VHH or fusion protein.

Immunoconjugates of the Invention

A further aspect of the invention relates to an immunoconjugate comprising the VHH according to the invention conjugated to at least one chemical compound.

The immunoconjugate of the invention results from the chemical coupling of the VHH to the chemical compound, either directly or optionally via a linker, to form a conjugate. Mutation of the VHH to introduce a supplementary cysteine in the sequence, preferably but not exclusively at the C-terminus is envisioned as an easy way to couple chemical compounds to the VHH.

Such conjugate is therefore obtained by coupling (either by covalent or non-covalent coupling) of the VHH with the chemical compound, optionally via a linker.

The covalent linkage between the VHH and the chemical compound is typically obtained via the use of a coupling or cross-linking agent, and optionally a linker for covalent linkage of both molecules while maintaining their functionality, or allowing cleavage. A variety of coupling or cross-linking agents can be used for making the immunoconjugates of the invention. Examples of cross-linking agents include carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g. Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78,1 18-132; Brennan et al., 1985 Science 229:81-83), and Glennie et al., 1987 J. Immunol. 139: 2367-2375). Examples of linker types include, but are not limited to, hydrazones, thioethers, esters, disulfides and peptide-containing linkers. A linker can be chosen that is, for example, susceptible to cleavage by low pH within the lysosomal compartment or susceptible to cleavage by proteases.

Typically, the chemical compound is a therapeutic chemical compound.

As used herein, the term "therapeutic chemical compound" refers to any chemical compound that can be administered to a patient to produce a beneficial therapeutic or diagnostic effect though binding to and/or altering the function of a biological target molecule in the patient. The target molecule can be an endogenous target molecule encoded by the patient's genome (e.g., an enzyme, receptor, growth factor, cytokine encoded by the patient's genome) or an exogenous target molecule encoded by the genome of a pathogen (e.g., an enzyme encoded by the genome of a virus, bacterium, fungus, nematode or other pathogen).

Typically, therapeutic chemical compound include but are not limited to immunosuppressive agents (e. g., cyclosporin A, rapamycin, FK506, prednisone), antiviral agents (acyclovir, ganciclovir, indinavir), antibiotics (penicillin, mynocyclin, tetracycline), anti-inflammatory agents (aspirin, ibuprofen, prednisone), cytotoxins or cytotoxic agents (e. g., paclitaxel, cytochalasin B, gramicidin D, ethidium bromide, emetine, mitomycin C, etoposide, tenoposide, vincristine, vinblastine, colchicine, doxorubicin, daunorubicin, dihydroxy anthracindione, mitoxantrone, mithramycin, actinomycin D, 1-dihydrotestosterone, glucocorticoids, procaine, tetracaine, lidocaine, propranolol, puromycin, and analogs or homologs of any of the foregoing agents. Suitable drugs also include antimetabolites (e.g., methotrexate, 6-mercaptopurine, 6-thioguanine, cytarabine, 5-fluorouracil decarbazine), alkylating agents (e. g., mechlorethamine, thioepachlorambucil, CC-1065, melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e. g., daunorubicin (formerly daunomycin) and doxorubicin), antibiotics (e. g., dactinomycin (formerly actinomycin), bleomycin, mithramycin, and anthramycin (AMC)), radionuclides (e. g., iodine-125,-126) yttrium (e. g., yttrium-90,-91) and praseodymium (e.g., praseodymium-144,-145), and protease inhibitors (e.g., inhibitors of matrix metalloproteinases).

In one embodiment, therapeutic chemical compound include but are not limited to analgesic agents, including narcotics (e.g., codeine, nalmefene, naloxone, fentanyl, meperidine, morphine, tramadol, propoxyphene, oxycodone, methadone, nalbuphine), nonsteroidal anti-inflammatory agents (e. g., indomethacin, ketorolac, arthrotec, ibuprofen, naproxen, salicylate, celecoxib, rofecoxib), acetaminophen, capsaicin, and ziconotide.

In a particular embodiment, the therapeutic chemical compound is a therapeutic nucleic acid such as antisense nucleic acids and RNAi.

Diagnostic Methods and Uses of the Invention

The fusion proteins of the invention may be particularly suitable for diagnostic purposes.

In particular, a fusion protein of the invention is used in a method of diagnosis an infectious disease in a patient in need thereof.

Therefore, a further aspect of the invention relates to the fusion protein for use in a method of detecting in vitro the presence of infectious agents in a patient in need thereof.

The term "patient" refers to human. Preferably, the patient refers to human afflicted with infectious diseases.

In a particular embodiment, the method of the invention may be performed by red blood cell agglutination assays.

Typically, the present invention relates to a red blood cell agglutination assay for the detection of immunization against infectious agents in a blood sample, comprising the steps consisting of:

i) bringing the blood sample into contact with the fusion protein according to the invention, and ii) concluding that immunization against the infectious agent is present in the patient when the red blood cells are agglutinated, or concluding that immunization is absent or present at a low level in the patient when the red blood cells are not agglutinated.

In some embodiments, the red blood cell agglutination may be determined by any well-known method in the art and typically involves red blood cell agglutination assay such as described in the prior art (7-9). Typically a red blood cell agglutination assay as described in the EXAMPLE is used for determining the red blood cell agglutination.

Typically, the fusion protein of the invention induces red blood cell agglutination if patient's blood sample contains antibodies directed against the fused antigen. In the case of patient infected by infectious agent, antibodies directed against said infectious antigen and present in patient's blood sample will recognize and bind the antigens of the fusion proteins, the VHH of said fusion protein directed against GPA also bound to red blood cells and therefore induces their agglutination.

In another embodiment, the fusion protein of the invention induces red blood cell agglutination if patient's blood sample contains infectious agents capable of being bound by the fused antibody. In this case, infectious agent present in patient's blood sample will be recognized and bound by the antibody of the fusion proteins directed against the infectious agent, the VHH of said fusion protein directed against GPA binds to red blood cells and therefore induces their agglutination.

In another embodiment, the VHH of the present invention may be used in a method of detecting recombinant polypeptide, particularly, recombinant polypeptide having a tag sequence YPPE.

Typically, the VHH of the present invention may be used in preparative and analytical methods such as affinity chromatography, histochemistry, flow cytometry, and Fluorescence-activated cell sorting (FACS), subcellular localization, ELISA, western blotting or yet other immunoanalytical methods.

Therapeutic Methods and Uses of the Invention

The fusion protein or the immunoconjugate of the invention may be used in a method of treating diseases in a patient in need thereof.

Therefore, a further aspect of the invention relates to the fusion protein or the immunoconjugate of the invention for use as a medicament.

In one embodiment, the fusion protein or the immunoconjugate according to the invention may also be used to increase the half-life of the fused heterologous polypeptide or the conjugated chemical compound of the invention in the systemic circulation.

In one embodiment, the present invention relates to the fusion protein or the immunoconjugate according to the invention for use in a method of increasing therapeutic polypeptide or therapeutic chemical compound serum half-life in a patient in need thereof.

The expression "increasing therapeutic polypeptide or therapeutic chemical compound serum half-life" refers to the enhancing therapeutic compound serum half life in vivo by protecting the therapeutic compound against degradation or elimination from the circulation. Therapeutic polypeptides or therapeutic chemical compounds with increased serum half-life are therapeutic compounds that resists from degradation or removal by endogenous mechanisms which remove unwanted material from the organism.

In one embodiment, the present invention relates to a method of increasing therapeutic polypeptide or therapeutic chemical compound serum half-life in a patient in need thereof, comprising the step of administering to said patient the fusion protein or the immunoconjugate according to the invention.

Pharmaceutical Compositions and Kits of the Invention

The invention also relates to a pharmaceutical composition comprising the fusion protein or the immunoconjugate of the invention.

Therefore, fusion protein or immunoconjugate of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce any adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for an intravenous or systemic administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the fusion protein or the immunoconjugate may be dissolved or dispersed in a pharmaceutically acceptable carrier or aqueous medium.

The pharmaceutical forms suitable for injectable use include sterile aqueous solutions; formulations including sesame oil, peanut oil or aqueous propylene glycol; and sterile powders for the extemporaneous preparation of sterile injectable solutions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Under ordinary conditions of storage and use, these preparations contain a preservative to prevent the growth of microorganisms.

A fusion protein or an immunoconjugate of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the required amount of the active compounds in the appropriate solvent with various/several of the other ingredients enumerated above, as required, followed by filtered sterilization. Generally, dispersions are prepared by incorporating the various sterilized active ingredients into a sterile vehicle which contains the basic dispersion medium and the other required ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above.

For administration in an aqueous solution, for example, the solution should be suitably buffered if necessary and the liquid diluent first rendered isotonic with sufficient saline or glucose. These particular aqueous solutions are especially suitable for intravenous administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The fusion protein or the immunoconjugate of the invention may be formulated within a therapeutic mixture to comprise about 0.0001 to 1.0 milligrams, or about 0.001 to 1.0 milligrams, or about 0.01 to 1.0 milligrams, or about 0.1 to 1.0 milligrams or even about 10 milligrams per dose or so. Multiple doses can also be administered.

In certain embodiments the VHHs of the invention are contemplated to be used for the assembly of immunoliposomes. Such red cells targeted immunoliposomes might be useful to selectively deliver specific cargo to pathological red cells: as an example one may imagine to deliver to red cells of sickle cells disease drugs which might interfere with HbS polymerization or with adhesion molecules phosphorylation since these molecular events are known to be important in acute complications of the disease (El Nemer W, Colin Y, Le Van Kim C. Role of Lu/BCAM glycoproteins in red cell diseases. Transfus Clin Biol. 2010 September; 17(3):143-7).

Liposomes are formed from phospholipids that once dispersed in an aqueous medium spontaneously form multilamellar concentric bilayer vesicles (also termed multilamellar vesicles (MLVs)). MLVs generally have diameters ranging from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention also provides kits comprising at least one fusion protein or immunoconjugate of the invention. Kits containing fusion protein or immunoconjugate of the invention find use in therapeutic or diagnostic methods.

| VHH sequences |
| --- |
| SEQ ID NO: 1 for CDR1:<br>SGYTDSTYCVG |
| SEQ ID NO: 2 for CDR2:<br>RINTISGRPWYADSVKG |
| SEQ ID NO: 3 for CDR3:<br>TTANSRGFCSGGYNY |
| SEQ ID NO: 4 for CDR1 of 2cPCR51 VHH:<br>SGYTYSTYCVG |
| SEQ ID NO: 5 for CDR2 of 2cPCR51 VHH:<br>PINTVGDTPWYADSVKG |

-continued

VHH sequences

SEQ ID NO: 6 for CDR3 of rcPCR18 VHH:
TTANSRGLCSGGYNY

SEQ ID NO: 7 for IH4:
QVQLQESGGGSVQAGGSLRLSCVASGYTDSTYCVGWFRQAPGKEREGVAR
INTISGRPWYADSVKGRFTISQDNSKNTVFLQMNSLKPEDTAIYYCTLTT
ANSRGFCSGGYNYKGQGQVTVS SEQ ID NO: 8 for rcPCR25:
QVQLQESGGGSVQAGGSLRLSCVASGYTDSTYCVGWFRQAPGKEREGVAR
INTISGRPWYADSVKGRFTISQDNSKNAVFLQMNSLKPEDTAIYYCTLTT
ANSRGFCSGGYNYKGQGQVTVS SEQ ID NO: 9 for 2cPCR21:
QVQLQESGGGSVQAGGSLRLSCVASGYTDSTYCVGWFRQAPGKEREGVAR
INTISGRPWYADSVKGRFTISQDNSKNTVFLQMNSLKPEDTAIYHCTLTT
ANSRGFCSGGYNYKGQGQVTVS SEQ ID NO: 10 for 2cPCR56:
QVQLQESGGGVVQAGGSLRLSCVASGYTDSTYCVGWFRQAPGKEREGVAR
INTISGRPWYADSVKGRFTISQDNSKNTVFLQMNSLKPEDTAIYYCTLTT
ANSRGFCSGGYNYKGQGQVTVS SEQ ID NO: 11 for rcPCR07
QVQLQESGGGVVQPGGSLRLSCVASGYTDSTYCVGWFRQAPGKEREGVAR
INTISGRPWYADSVKGRFTISQDNSKNTVFLQMNSLKPEDTAIYYCTLTT
ANSRGFCSGGYNYKGQGQVTVS SEQ ID NO: 12 for 2cPCR11:
QVQLQESGGGSVQAGGSLRLSCVASGYTDSTYCVGWFRQAPGKEREGVAR
INTISGRPWYADSVKGRFTISQDNSKNTVFLQMNSLKPEDTAIYYCTLTT
ANSRGFCSGGYNYKGQGQVTVS SEQ ID NO: 13 for rcPCR26:
QVQLQESGGGSVQAGGSLRLSCVASGYTDSTYCVGWFRQAPGKEREGVAR
INTISGRPWYADSVKGRFTISQDNSKNTVFLQMNSLKPEDTAIYYCTLTT
ANSRGFCSGGYNYKGQGQVTVS SEQ ID NO: 14 for 2cPCR27:
QVQLQESGGGSVQAGGSLRLSCLASGYTDSTYCVGWFRQAPGKEREGVAR
INTISGRPWYADSVKGRFTISQDNSKNTVFLQMNSLKPEDTAIYYCTLTT
ANSRGFCSGGYNYKGQGQVTVS SEQ ID NO: 15 for rcPCR18:
QVQLQESGGGSVQAGGSLRLSCVASGYTDSTYCVGWFRQAPGKEREGVAR
INTISGRPWYADSVKGRFTISQDNSKNTVFLQMNSLKPEDTAIYYCTLTT
ANSRGFCSGGYNYKGQGQVTVS SEQ ID NO: 16 for 2cPCR51:
QVQLQESGGGSVQAGGSLRLSCVASGYTYSTYCVGWIRQAPGKEREGVAP
INTVGDTPWYADSVKGRFTISQDNSKNTVFLQMNSLKPEDTAIYYCTLTT
ANSRGFCSGGYNYKGQGQVTVS SEQ ID NO: 17 for epitope:
YPPE The invention will be further illustrated by the following figures and examples.

However, these examples and figures should not be interpreted in any way as limiting the scope of the present invention.

FIGURES

FIG. 1: Flow cytometry analysis of IH4 interaction with red cells.

Panel A shows that red cells do interact with IH4 irrespective of the M and N blood group antigens carried by GPA. Code used for identification of the tracings is indicated at the bottom of the panel, Negative control (obtained by incubating cells only with anti-HA antibody and tagged anti-mouse IgG Fab) corresponds to the gray filled histogram.

Panel B and C show flow cytometry results obtained with M+N+ red cells treated with different concentrations of trypsin (indicated at the bottom of the panels) before incubation with $V_HH$ or antibody. Results of Panel B cells have been obtained with IH4: MFI does increase with increasing concentrations of trypsin (indicated at the bottom of the panel). Results of panel C have been obtained with a commercial anti-GPA+B murine antibody: MFI does decrease with increasing concentrations of trypsin. Negative controls correspond to the gray filled histograms.

Figure 2:
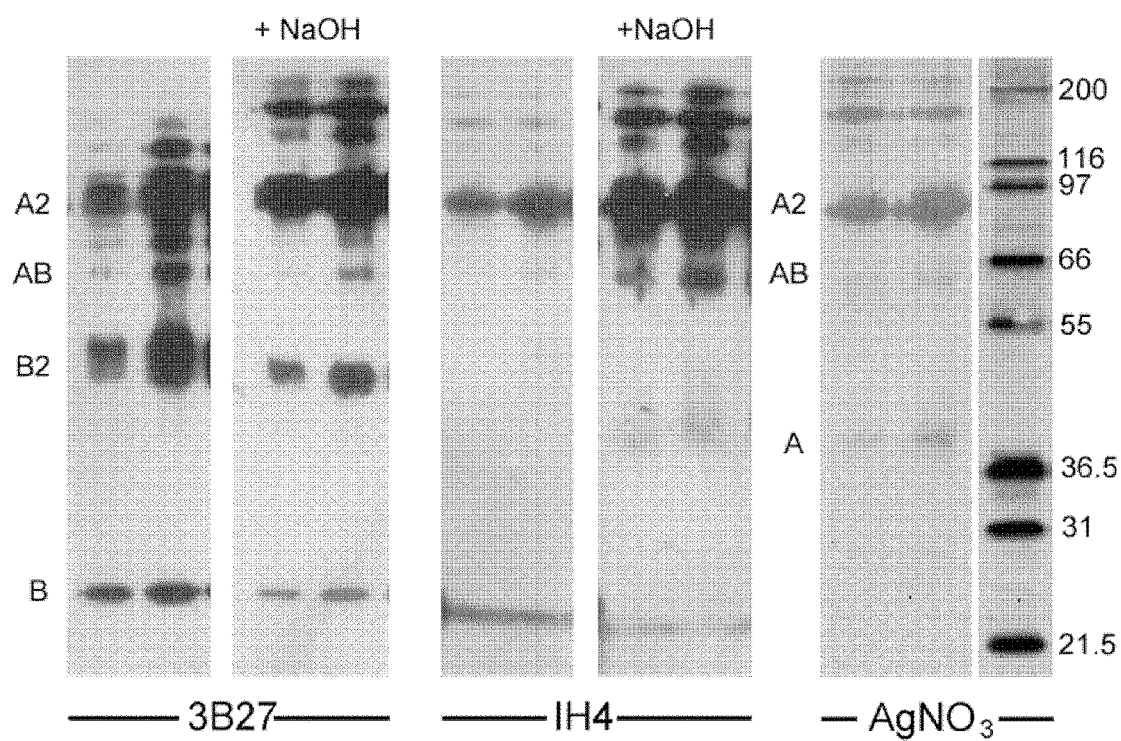

FIG. 2: Effect of beta elimination of sugars carried by GPA on reactivity of IH4 with GPA.

Crude glycophorins mixture was used for SDS-PAGE run on 12.5% gels. Panel at the right of the figure shows silver nitrate stained gel (the three lanes were loaded with respectively from left to right 2.5 and 5 µg of glycophorins and molecular weight standards) while other panels are western blots probed with the anti-GPB+A murine monoclonal 3B27 (6) or IH4 as indicated at the bottom of the figure (two amounts of glycophorins have been loaded: 1.25 and 2.5 µg). Molecular weights of markers are indicated in the margins of the figure as well as positions of monomeric GPA (A), GPB (B), homo (A2 and B2) and heterodimer (AB). Large molecular weight bands above A2 dimer correspond to glycophorins oligomers. Sodium hydroxide treatment of PvDF membrane lowers reactivity of 3B27 to GPB, while reactivity of IH4 towards GPA is noticeably increased (note that monomeric GPA and heterodimer AB are revealed only on the NaOH treated blot).

Figure 3:
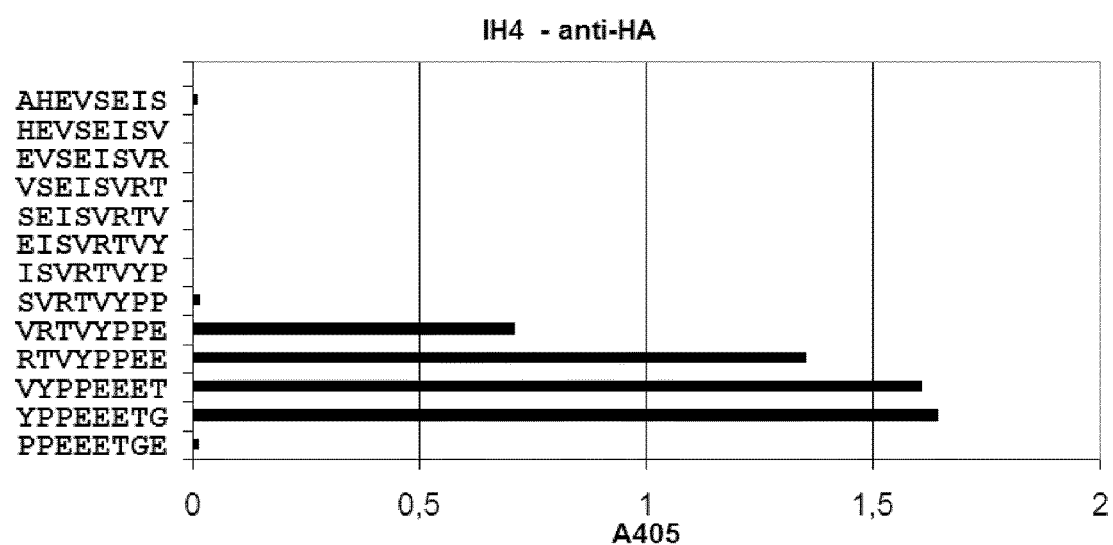

FIG. 3: Pepscan analysis of CA52 reactivity

Binding of IH4 to octapeptides overlapping the GPA sequence from $A_{40}$ to $E_{60}$, synthesized at the tip of plastic pins was detected with anti-HA tag antibody and peroxidase-tagged anti-mouse antibody). Only peptides containing YPPE sequence do show any binding of IH4.

Figure 4:
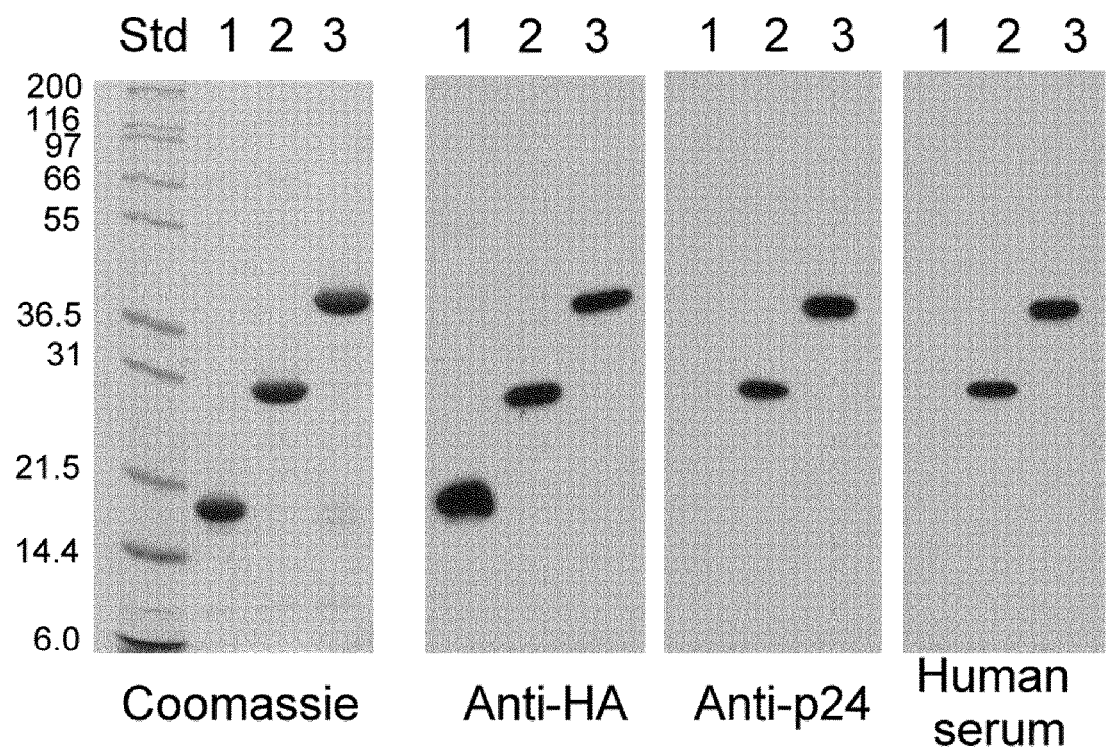

FIG. 4: SDS-PAGE and western blot of IH4 and p24 containing constructs.

SDS-PAGE was performed in a 15% gel. Protein in the gel was either stained with Coomassie blue or transferred to a membrane which was revealed with antibodies or serum as indicated at the bottom of the figure. Lane marked Std was loaded with molecular weight standards, lanes marked 1 were loaded with purified IH4, lanes 2 were loaded with the p24 construct while lanes 3 were loaded with the bivalent IH4-p24 construct.

Figure 5:
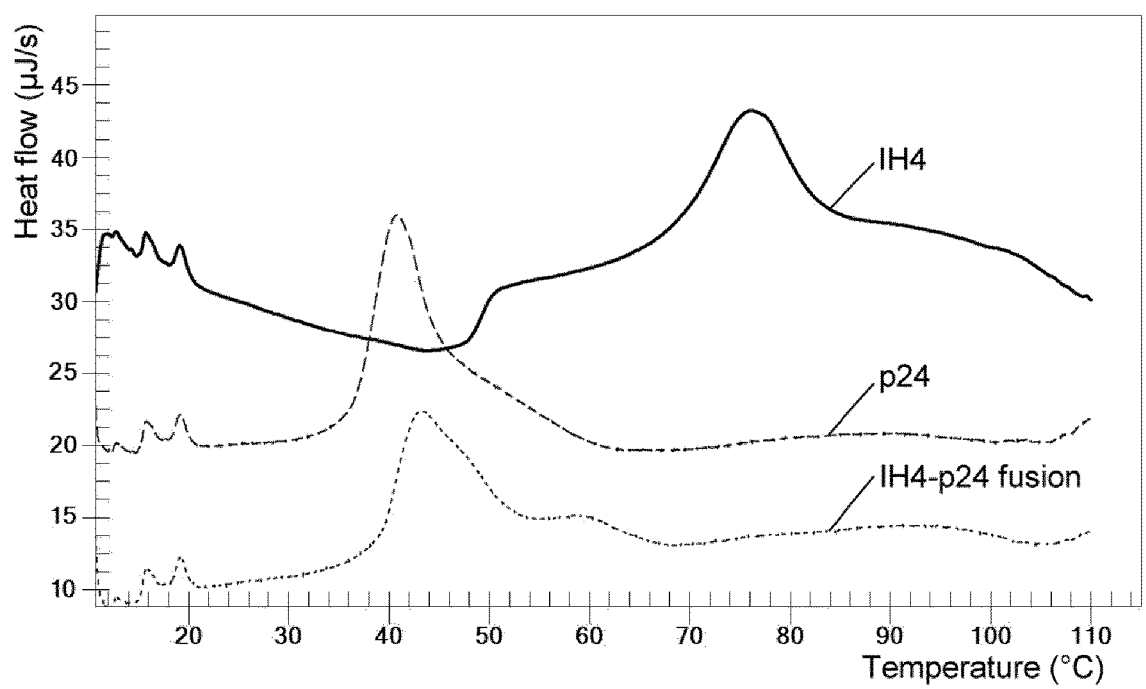

FIG. 5: Differential scanning calorimetry.

Records obtained with IH4, p24 and IH4-p24 fusion. For clarity, curves are off-set on the y-axis.

Figure 6:
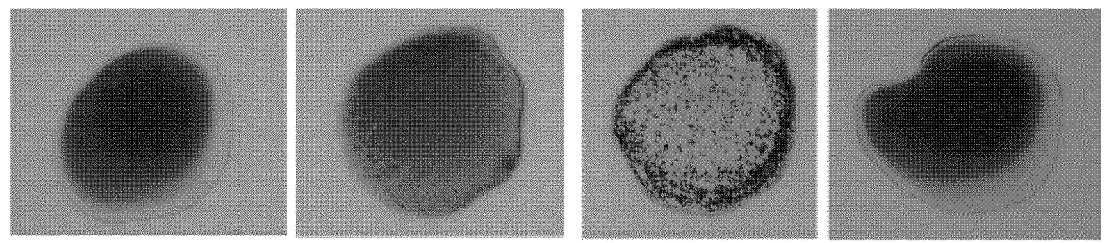
Figure 6:
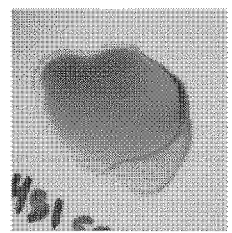
Figure 6:
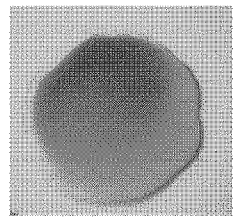
Figure 6:
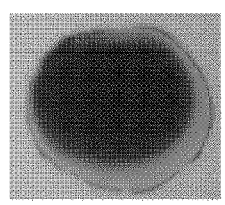

FIG. 6: Agglutination experiments using reconstituted blood prepared from a HIV positive serum sample, and controls.

Concentrations of IH51 (IH4-p24 fusion), IH4 and isolated p24 are indicated below each picture of the flattened drops. Upper and median row are results obtained with reconstituted blood prepared from a HIV-positive serum while drop on lower row was obtained with reconstituted blood prepared from plasma of a non-infected person. Picture was taken after 2 minutes of incubation.

Figure 7:
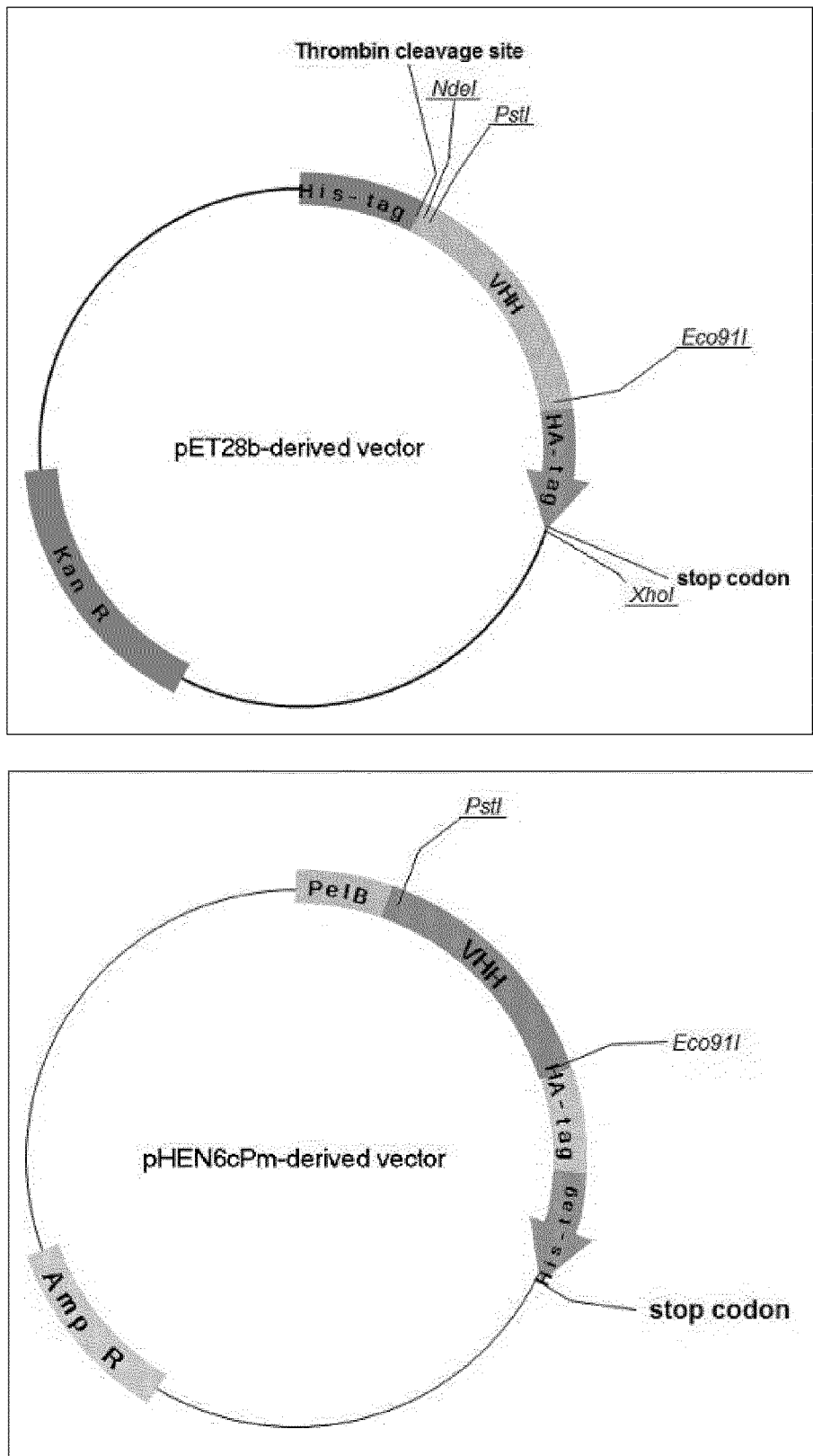

FIG. 7: Cartoon of the two plasmids used for expression of VHH.

Positions of restriction enzymes sites which have been used in this study are indicated.

Figure 8:
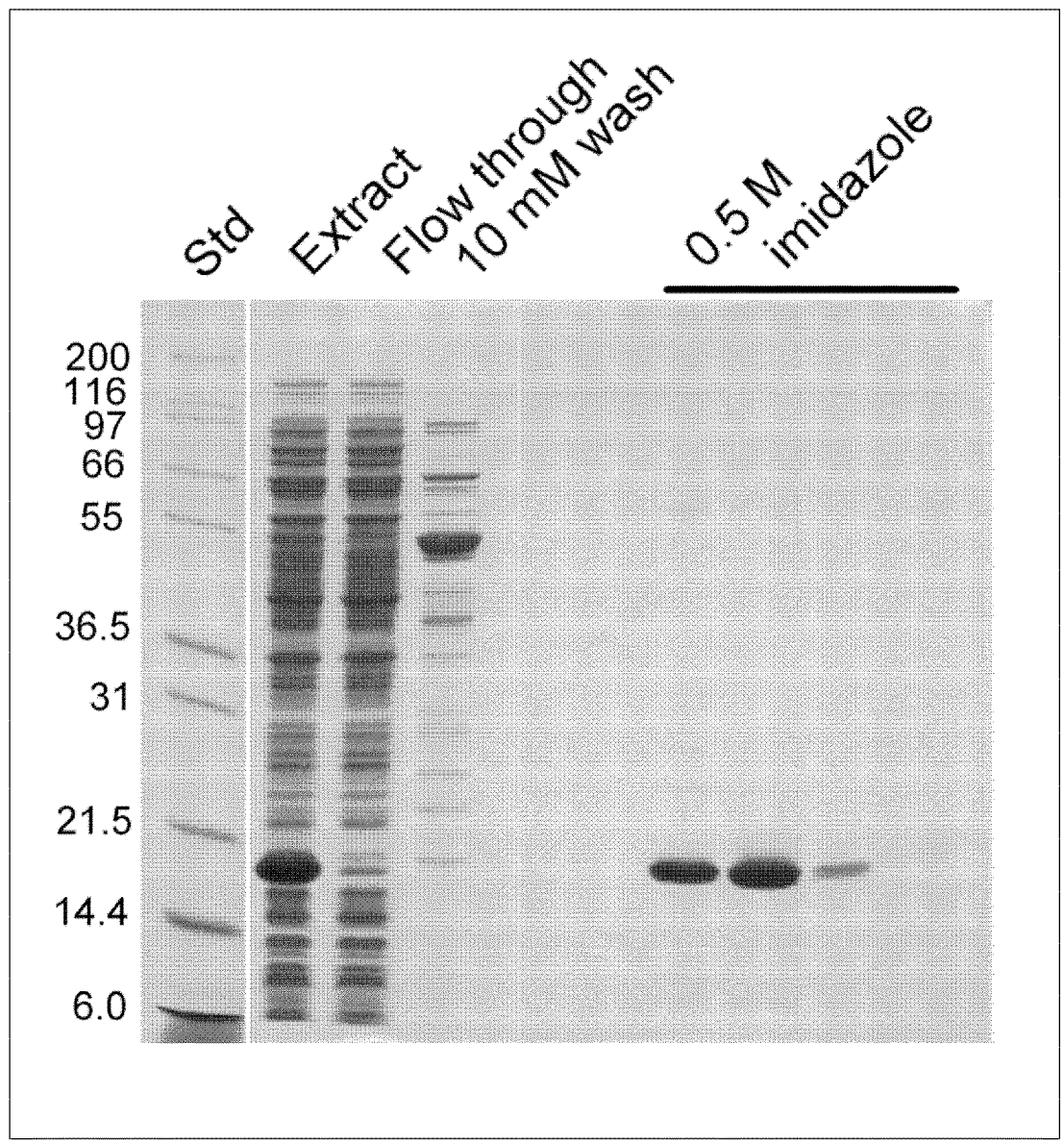

FIG. 8: Purification of IH4 expressed in SHuffle cells on an immobilized cobalt column.

Coomassie stained 15% acrylamide SDS-PAGE. Lanes were loaded as indicated on top of the gel. Std is for molecular weight standard, (molecular weights are indicated on the left of the figure). Lane marked extract was loaded with 10 µl of clarified extract. Lane marked Flow through was loaded with 10 µl of pooled fractions corresponding to unretained material. Peak eluted from column through 10 mM Imidazole was pooled and loaded onto the gel (10 mM wash). Aliquots of 0.5 M imidazole eluted fractions correspond to $\frac{1}{10000}^{th}$ of each fraction (fraction volume: 5 ml)

Figure 9:
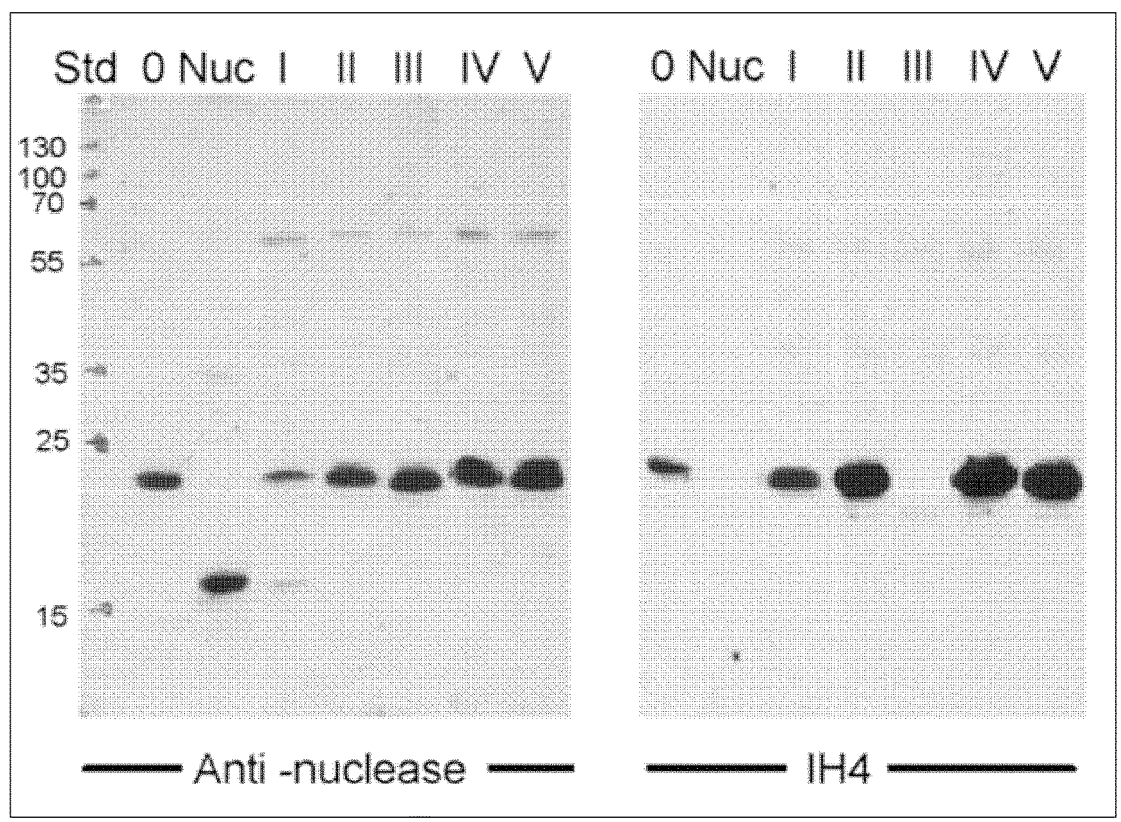

FIG. 9: Western blot probed with IH4 of diverse constructs consisting of the extracellular domain of GPA fused to *Staphylococcus aureus* nuclease and deletion mutants of it.

Western blot revealed by anti-nuclease antiserum or IH4 as indicated. Nature of samples loaded is indicated on top of the blots: Std indicates that a stained molecular weight standard has been loaded in this lane (position of bands has been pointed and theoretical molecular masses indicated on the left of the blot). Nuc indicates that *Staphylococcus aureus* nuclease has been loaded in the lane. For the codes of other lanes refer to panel A.

Figure 10:
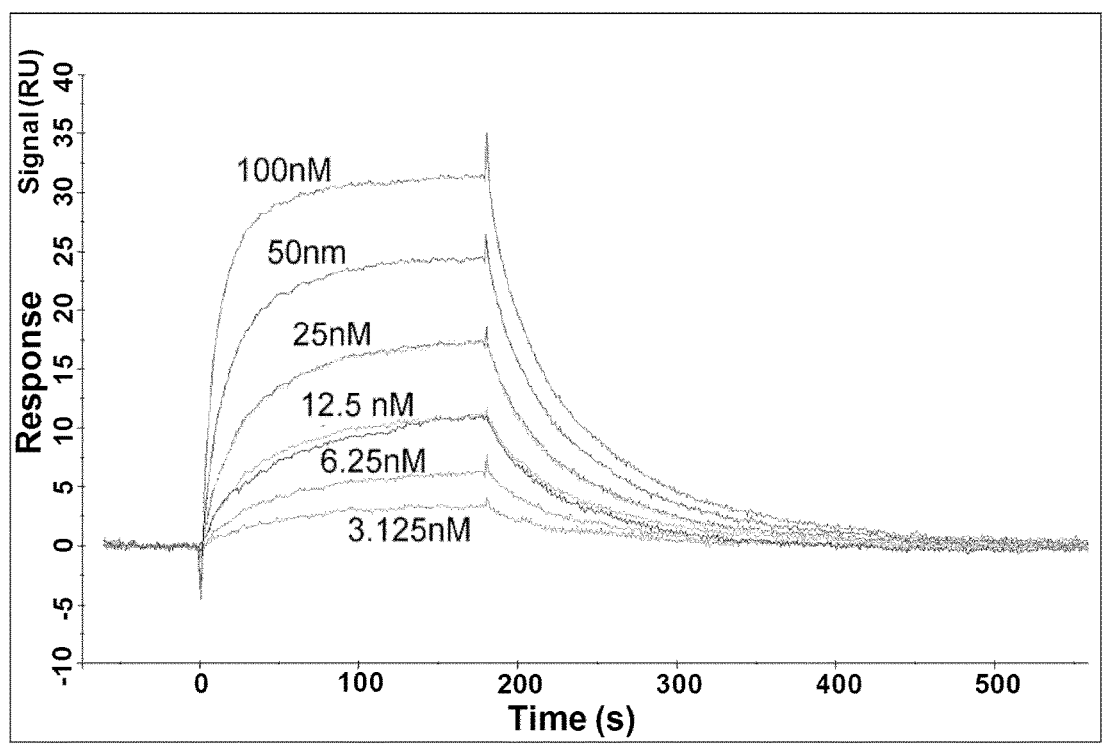

FIG. 10: Sensorgram showing interaction of IH4 with glycophorin A.

SPR recordings obtained in a Biacore X100 apparatus. Purified Glycophorin A was immobilized at 400 resonance units on Fc2, reference channel Fc1 has been only activated and deactivated. Concentrations of IH4 injected are indicated on the figure.

Figure 11:
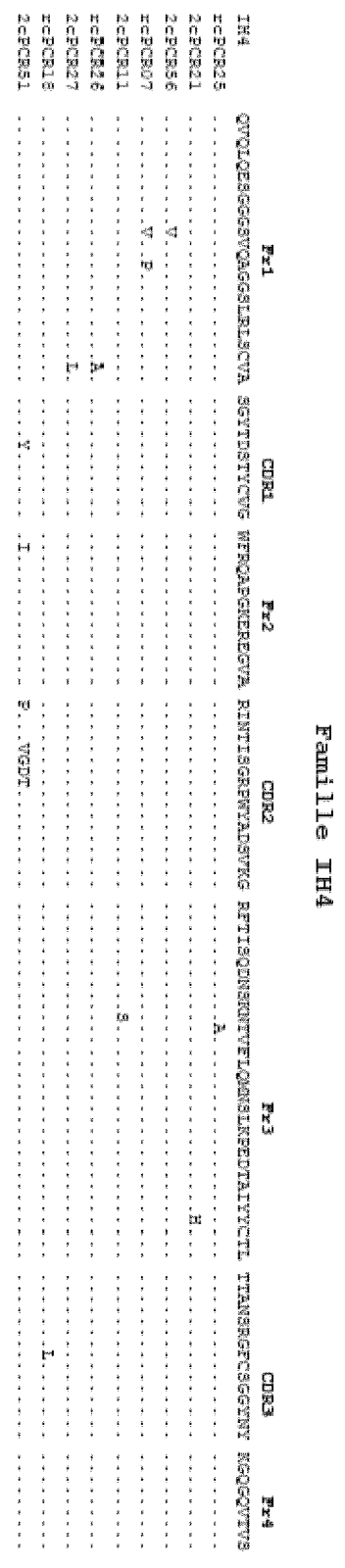

FIG. 11: VHHs Sequence alignment.

Multiple sequence alignment of VHHs amino acids sequences.

EXAMPLE

Material & Methods

Immunization of the Dromedary

Red cells of two different human donors were pooled in order to present the most complete array of blood group antigens. The packed red cells (300 ml) were transfused in a young female dromedary through jugular puncture. Transfusion was completed in approximately one hour time and went on without other adverse effect to the animal than transient tremulation. 7 and 14 days later 30 ml of the same red blood cells pools were injected subcutaneously without any clinical symptom.

Preparation of the Antigens Used for Library Panning

Purified glycophorin A was used for panning. It was prepared essentially as published (10): In short, red cell membranes washed in 5 mM phosphate buffer pH 8.0 were suspended in an equal volume of the same buffer supplemented with NaCl at 0.6 M final concentration. To this suspension, 9 volumes of chloroform methanol mixture (2:1 v:v) were added and suspension was shaken for 30 min at room temperature and then let to stand in the cold room overnight. The aqueous phase containing essentially a mixture of glycophorins (glycophorins A, B C and D) was recovered and clarified by centrifugation for 30 min at 40,000 g in a JA 20 Beckman rotor. The clarified supernatant was dialyzed against several changes of 5 mM ammonium carbonate pH 8.3 and finally lyophilized. Highly pure glycophorin A was obtained by reverse phase liquid chromatography performed in a C18 column operated with trifluoroacetic acid acetonitrile water mobile phases. Carboxymethylation of the crude glycophorins mixtures prior to HPLC (and hence of Cys50 of GPB present at the interface of the GPB-GPA dimer) effects in disruption of the GPA-GPB heterodimers and enables obtaining homogenous, GPB-free, GPA (10).

Preparation of the Library

One week after the last subcutaneous injection of human red cells, 100 ml blood was drawn from the dromedary, lymphocytes were isolated and the library was prepared according to established methods ((11-12) and references cited therein). Vector for library preparation was pHEN4 vector, it is coding for a PelB signal sequence, the cloned $V_HH$ followed by the HA-tag, and then downstream an Amber stop codon the gene for the M13 bacteriophage protein PIII. Cells used for library preparation and subsequent pannings were TG1 cells allowing ribosomes reading through the Amber stop codon to produce VHH-PIII fusions.

Screening of the VHH Library

The human red cells immunized dromedary's VHH library was screened using phage display. To capture the $V_HH$-displaying phages, glycophorin A was used. Protein was coated overnight at 4° C. in the capture well (100 µl of a 100 µg/ml solution in PBS) of a high-binding 96-well ELISA plates (Costar, Corning, Cherges, France). A control well was left uncoated. Following morning the capture and control wells were washed 3 times with PBS containing 0.05% Tween and blocked with 2% skimmed milk in PBS for 1 hour at room temperature. Then, phages prepared from the library in presence of helper phage M13K07 (New England Biolabs, Ipswich, Mass. USA) were incubated for 1 hour at room temperature in antigen-captured and control wells. Wells were washed 5 times with PBST and phages eluted through alkaline triethylamine solution. Phages eluted from the capture well were amplified after rescue with M13K07 helper phage in order to allow performing three consecutive rounds of panning. After each of the 3 panning rounds phages eluted from the capture well and from the control well were serially diluted and used to infect *E. coli* TG1-strain permissive cells. The dilutions were then plated onto Petri dishes allowing an evaluation of the antigen-specific phage enrichment. Several clones derived from the positive well were grown in liquid media (1 ml Terrific Broth) and used to prepare periplasmic extracts (PE) for ELISA to check for expression of GPA reactive VHH.

ELISA Pepscan Analysis

ELISA plates (high-binding plates; Costar, Corning, Cherges, France) were coated overnight with antigen (10 µg/mL, 100 µL/well). For blocking and washing, respectively, 1% skimmed milk and 0.05% Tween-20 in phosphate-buffered saline were used respectively. Each plate was probed with $V_HH$ samples (either PE or purified protein, at 0.1-10 µg/mL incubated 1 hour at room temperature); a positive control was also loaded on each plate (an anti-DARC VHH (13) either purified, or prepared as a periplasmic extract, it was incubated in a DARC-coated well) and a negative control (periplasmic extract prepared from uninfected TG1 or a purified unrelated $V_HH$ incubated in a glycophorin coated well). Bound $V_HH$s were revealed with murine anti-HA antibody (HA.11 clone 16B12, Covance, Brussels, Belgium) and alkaline phosphatase-tagged anti-mouse antiserum (Sigma, l'Isle d'Abeau, France); an i-Mark BioRad microplate reader (Marnes-la-Coquette, France) recorded the color developing from the phosphatase substrate (Sigma).

The binding of purified IH4 to immobilized peptides was studied using general methods similar to those of ELISA (13-14). Briefly, octapeptides covering GPA sequence from $A_{40}$ to $E_{60}$ were synthesized at the tips of plastic pins. The pins were first blocked in Tris buffered saline (TBS) containing 2% bovine serum albumin. The pins are arranged according to the format of a 96 wells plate so all incubations can be done using ELISA plates. Pins after blocking were incubated overnight with purified IH4 (50 ng/mL in TBS containing 0.05% Tween 20) and then washed. Finally IH4 binding was appreciated by means of the Covance anti-HA murine antibody and Alkaline phosphatase tagged rabbit antimouse IgG (Dako, Glostrup Denmark). Last step was dipping the pins into phosphatase substrate and appreciating color development using an ELISA reader. Between each step the pins were washed in TBS 0.05% Tween 20. Final results are presented as differences of readings obtained with IH4 followed by anti-HA and tagged antimouse antibody and those obtained with only anti-HA followed by tagged anti-mouse.

VHH Subcloning, Expression and Purification

Two vectors shown in FIG. 7 were used for subcloning with the same set of restriction enzymes for both vectors (PstI and Eco91I-Fermentas Thermo Scientific Illkirch France). These restriction sites are situated in frameworks 1 and 4 respectively and are preceded and followed respectively by sequences coding for 4 conserved N-terminal and 3 C-terminal residues of VHH. pHEN6cPm (13) codes for a Pel B sequence, the $V_HH$, an HA tag and finally a polyhistidine tail. The pEt28-b vector obtained from Novagen (Merck Darmstadt FRG) was modified to allow easy subcloning of $V_HH$s with the same restriction enzymes PstI and Eco91I as follows: First, unique Eco91I restriction site present in Lad gene was mutated using QuikChange kit (Stratagene, Agilent Santa Clara Calif. USA) (a silent mutation was introduced disrupting the restriction site). Then, starting from a pHEN6cPm plasmid harbouring a VHH, the fragment coding for VHH followed by HA tag (and stop codons) was amplified, adequately digested, and ligated into Nde1- and Xho1-digested mutated pET28-b. Resulting plasmid is coding for, from 5' to 3', a polyhistidine tail, a thrombin cleavage site, the $V_HH$ and finally an HA-Tag. This vector is used for routine sub cloning of other $V_HH$ using the PstI and Eco91I sites.

The pHEN6cPm vector drives $V_HH$ expression in periplasm. Cells used for expression of pHEN6cPm coded $V_HH$ were BL21 purchased from Stratagene. Expression in periplasmic space of BL21 cells was performed by inoculating 330 ml of TB medium present in a 1 liter shake flask with 3 side baffles. When optical density of bacterial culture reached 0.8 to 1.2 production was induced by adding Isopropyl thiogalactoside at 1 mM final concentration and fermentation let to proceed at 27° C. for 18 hours. Periplasmic extract was prepared by suspending bacterial pellet (corresponding to 330 ml fermentation volume) in 60 ml TES buffer (0.2 M Tris 0.5 mM EDTA 0.5 M sucrose pH8.0) shaking in the cold for 1 hour then diluting with 90 ml of TES buffer diluted to the fourth with water and incubating again for 1 hour. Periplasmic extract was recovered by centrifugation, SDS-PAGE was used to check that $V_HH$ was present in the supernatant, and pellet was discarded.

The pET28 derived vector was used for intracytoplasmic expression. Cells used for expression of $V_HH$ in pET28 vector were SHuffle C3029H cells purchased from New England Biolabs. These cells are engineered to facilitate cytoplasmic expression of disulfide bonded proteins. Expression in cytoplasm of SHuffle cells was obtained by inoculating 330 ml of LB medium present in a 1 L shake flask with 3 side baffles and incubation at 30° C. When optical density of fermentation medium reached 0.4 to 0.8 production was induced by adding Isopropyl thiogalactoside at 0.1 mM final concentration temperature was lowered to 20° C. and fermentation let to proceed for 24 hours. Pelleted cells resuspended in 60 ml of PBS containing 0.3M NaCl were broken by three passages in an Emulsiflex homogenizer (Avestin Ontario Canada) operated at 20000 psi. Extract was clarified by centrifugation.

$V_HH$ was purified from periplasmic or cytoplasmic extract using a cobalt-loaded Talon column (Clontech Mountain View Calif. USA). Dimensions of column suited to process $V_HH$ amount produced by 1 liter fermentation of SHuffle cells were 1.6 cm inner diameter for a height of 10 cm, flow rate was 2 ml/min, equilibration buffer was PBS with NaCl concentration increased to 0.3M (PBS-NaCl). After sample loading, column was rinsed first with PBS-NaCl then with PBS-NaCl containing 10 mM imidazole. $V_HH$ was eluted using PBS-NaCl containing 0.5 M imidazole. All buffers were supplemented with 1 mM PMSF. Purification from PE was performed similarly, but sample before sample loading and column equilibration buffer were supplemented with $MgCl_2$ at 5 mM final concentration. VHH eluted from the immobilized metal column was desalted onto a G25 column equilibrated in PBS or polished by chromatography on Superdex S70 GE Healthcare (Uppsala Sweden) column equilibrated in PBS.

Fusion of HIV p24 to IH4

Assaying antibodies against p24 is widely used to establish immunization against HIV (15). A synthetic gene encoding $V_HH$ C-terminus (3' from the Eco91I restriction site), then, in frame, residues 10 to 238 of HIV-1 gag protein (GenBank: AAD28912.1) an HA-tag and finally a stop codon was prepared by MwgBiotech (Ebersberg, FRG). Optimized codons for E. coli expression were used, construct was provided by the manufacturer as an insert in a common plasmid. The construct was retrieved through PCR and Eco91I and Xho1 sites added at the 5' and 3' ends of the amplicon. After digestion amplicon was ligated to the adequately digested and dephosphorylated pET28 derived plasmid containing IH4. Sequencing verified that no unwanted mutations had been introduced during the process. IH4-p24 fusion was expressed in SHuffle cell and purified from soluble cytoplasm extract similarly to what was described previously for IH4.

Preparation of Other E. coli Expressed Constructs

Soluble p24 for competition experiments was obtained by digesting plasmid coding for the IH4-p24 fusion through Eco91I and Pst I and adding a short synthetic oligonucleotide in place of excised whole $V_HH$ sequence. By doing so we obtained a p24 derivative containing in addition to the N-terminal polyhistag and thrombin site and the C-terminal HA-tag, some residues derived from the frameworks 1 and 4 of IH4 encoded by the plasmid used as starting material.

In order to study epitope location on extracellular domain of GPA the DNA sequence coding protein residues from Ser15 to His67 of mature protein was amplified from a plasmid available in the laboratory (16) and ligated to an early version of T7 plasmid coding for nuclease of Staphylococcus aureus (13). From this vector deletion mutants were obtained using adequate primers and Quikchange mutagenesis kit from Stratagene. Five 5 consecutive amino acids deletions were made encompassing GPA sequence from residue 40 to the $64^{th}$. Constructs were expressed in BL21 cells intracellularly as soluble proteins. Bacterial lyzates were loaded onto SDS-PAGE gels and blotted onto membranes which were probed with IH4 and anti-nuclease anti serum.

Flow Cytometry Experiments for Characterization of IH4

Reactivity of IH4 towards human red cells was studied using erythrocytes with the common different M N phenotypes obtained from the Centre National de Reference des Groupes Sanguins, (Paris, France). Cells were washed twice in PBS and resuspended with either: purified IH4 or as control anti GPA+B murine monoclonal antibody (10 µg/ml) (Clone E3 Sigma L'Isle d'Abeau France). The suspension was left at room temperature for 1 h. After incubation with the primary antibody, cells were washed twice in wash buffer and incubated for one additional hour in the presence of anti-HA monoclonal antibody (clone 16B9 as an ascitic fluid purchased from Covance, diluted 1:16,000). A control of red blood cells incubated with anti-HA alone was also prepared. Cells were washed again and then incubated in the dark at room temperature with anti mouse IgG FITC-tagged Fab (5 µg/ml in PBS 0.1% Bovine serum albumin solution -PBS-BSA-, Beckman Coulter, Villepinte, France). After a final wash step in PBS, cells were analyzed by digital high speed analytical flow cytometry. Erythrocytes were identified based on forward and side scatter characteristics using logarithmic amplification. Important dilution factor of anti-HA antibody and detection with FITC-conjugated Fab (as indicated above) provided for minimal agglutination of red cells. Excitation wavelength was 488 nm, FITC signal was collected with a 515/45 band pass filter. Data were acquired by BD FACS Diva software (v.6.1.2), and analyzed using FlowJo software v.7.2.5 (Treestar, Ashland, Oreg., USA).

In a second set of experiments red cells (suspended in PBS at 20% hematocrit) were treated with bovine trypsin (Sigma ref T1005) at concentrations varying from 75 µg/ml to 5 mg/ml for 20 minutes at 37° C. before being washed and analyzed by cytometry as described above.

Western Blots

Western blots of purified proteins or of aliquots taken at the purification steps was performed in a Novex semidry apparatus (Novex, Life Technologies Carlsbad Calif. USA). Membranes were either nitrocellulose (Schleicher and Schuell Dassel FRG) or PVDF (Millipore Agilent).

Antibodies used for revelation of transferred proteins were as needed anti HA 16 B9 clone, a rabbit anti-nuclease antiserum, (prepared in-house), Anti Poly Histidine murine monoclonal (Novagen) Anti p24 murine monoclonal (AB9071 AbCam Cambridge UK), Anti glycophorin B+A (3B27 clone (6)) and adequate secondary antibodies tagged with peroxydase. Chemiluminescent detection (ECL reagent kit GE Healthcare Uppsala Sweden) was used throughout.

Beta-elimination of sugars present on purified glycophorin was obtained on a PvDF membrane by incubating it in 55 mM NaOH for 16 hours at 40° C. then washing the membrane before probing with antibodies (17).

Surface Plasmon Resonance (SPR)

SPR analysis of $V_HH$ interactions used a Biacore X100 apparatus (GE Healthcare). Purified GPA was immobilized on a CM5 chip in the Fc2 channel to a level of 400 Resonance units using amine coupling chemistry as recommended by the manufacturer. Reference channel Fc1 was simply activated and deactivated through ethanolamine. 6 different concentrations of analyte were injected onto the chip for 180 seconds, and dissociation let to proceed for 600 seconds. Data were analyzed using BIA Evaluation software associated to the apparatus.

Differential Scanning Calorimetry

Experiments were performed in a Nano DSC apparatus (TA instruments New Castle Del. USA). Protein solutions were prepared at 1 mg/ml concentration in PBS. Heat flow was recorded as a function of temperature which was raised at 1° C./min from 12° C. to 110° C. Values measured with PBS alone were subtracted from values measured with proteins.

Agglutination Experiments

Testing for agglutination on glass tile was performed as follows: 50 µl of reconstituted blood (prepared by mixing one volume of patient or control serum with 1 volume of washed O Rh-washed red cells) was mixed on a glass tile with 50 µl of reagent containing in PBS BSA, either IH51 at concentrations varying from 100 µg/ml to 2 µg/ml, either IH51 and purified p24 (50 µg/ml), or IH4 at concentrations varying from 100 µg/ml to 2 µg/ml. Controls with PBS-BSA only were also prepared. The drops were mixed and flattened to the surface of a ca 1.5 cm diameter circle, glass tile was gently rocked back and forth and agglutination visually evaluated after 2 minutes and then photographed.

Results

Construction of $V_HH$ Library, Retrieval and Purification of IH4

The $V_HH$s amplified from circulating lymphocytes RNA of the dromedary immunized with human red blood cells were cloned into a library of $2.2 \times 10^8$ independent colonies of which 80% contain an insert in the phagemid with a size of a $V_HH$. After phage display and panning on purified GPA, 242 $V_HH$ clones out of 352 were identified that recognized the antigen specifically in PE ELISA. 208 bona fide $V_HH$ sequences were retrieved from colony PCR of positive clones. 30 different sequences were obtained they might be classified into 3 distinct families differing one from the other in the CDR3 region. The $V_HH$ (referred to as IH4) which is the subject of this report was found 140 times accounting then for 67% of the positively identified sequences. Multiple sequence alignment of VHHs amino acids sequences is shown on FIG. 11.

IH4 was expressed in periplasmic space of BL21 cells or in the cytoplasm of SHuffle cells and purified on an immobilized cobalt column. Yields of retrieved purified protein varied from 1 to 10 mg/liter fermentation medium in the case of periplasmic expression in BL21 while 90 to 120 mg/liter were obtained from expression in SHuffle cells. Protein produced from either cell was undistinguishable through characterization and functional studies described below. SDS PAGE of aliquots of fractions collected from the immobilized metal affinity columns are shown on FIG. 8.

Characterization of Recognized Epitope and Measurements of IH4 Affinity for GPA

IH4 does recognize GPA on red cells independently of blood group antigens carried by the molecule. This was established by flow cytometry using red cells of defined phenotypes. Results are shown on FIG. 1. Reactivity is similar whatever blood group phenotype M+N+M−N+ or M+N− (panel A).

Cytometry gave also an indication regarding epitope recognized by IH4: treatment of red cells with trypsin did increase somewhat mean fluorescence intensity (MFI) in a trypsin concentration dependent fashion, (FIG. 1 panel B) strongly suggesting that the recognized epitope is C terminally located to arginine 39, which together with arginine 31, is the preferential site for trypsin cleavage of GPA on red cells (6). Those tryptic cleavages remove most of the glycanic part of GPA and hence probably facilitate access of $V_HH$ to its cognate epitope. By contrast, reactivity of a commercial anti GPA+B monoclonal recognizing an epitope that is present on the N-terminal 29 residues common to both proteins, is significantly diminished upon trypsin treatment but not totally abolished since GPB remains undigested after incubation with trypsin (FIG. 1 panel C).

Beta-elimination of sugars on western blot membranes by alkaline treatment (17), likewise, demonstrates that reactivity of IH4 with GPA is increased when protein is freed from sugar chains (FIG. 2).

Western blot shown on FIG. 9 does show that E. coli expressed recombinant extracellular GPA fragment fused to

*Staphylococcus aureus* nuclease is recognized by IH4: this suggests that the epitope recognized on GPA is essentially formed by the polypeptide chain. Moreover studies of IH4 reactivity with deletion mutants of the extracellular domain showed that only one of the deletion mutants was not recognized narrowing down the identification of the epitope: clearly only deletion of the $T_{50}VYPP_{54}$ sequence of GPA abolishes interaction of IH4. Finally studies using peptides synthesized on plastic pins shown on FIG. 3 demonstrates that the recognized linear epitope comprises the $Y_{52}PPE_{55}$ sequence.

Affinity of IH4 for GPA was evaluated using SPR and purified GPA as ligand. Tracings are shown on FIG. 10. Data can be easily fitted using 1:1 Langmuir fit. $K_D$ is 33.72 nM (kinetic association constants ka and kd are respectively $5.73 \cdot 10^5$ $M^{-1}$ $s^{-1}$ and 0.019 $s^{-1}$).

Characterization of a p24-IH4 Bifunctional Derivative and of HIV1 p24

To evaluate how IH4 might be used as a building block of a reagent for an autologous erythrocyte agglutination assay, the inventors assembled a bifunctional derivative by fusing HIV-1 p24 to the C-terminus of IH4. Moreover isolated p24 construct was also prepared to be used as control in agglutination experiments. Fermentation in SHuffle cells, purification of IH4-p24 fusion (called IH51) or p24 construct was performed similarly as for IH4. Yields of IH51 and of isolated p24 were both in the range of 100 to 120 mg/Liter of fermentation medium. Lanes 2 and 3 on FIG. 4 show Coomassie stained SDS PAGE and western blots of respectively p24 and IH51.

As expected, purified proteins were recognized on western blot by murine anti p24 antibody, and the anti-HA tag antibody, moreover human serum known to contain anti-p24 antibodies did reveal isolated p24 construct (lanes 2 on FIG. 4) and the bifunctional IH4-p24 construct (lanes 3 on FIG. 4).

Differential scanning calorimetry of IH4 was repeated 8 times with identical results. The record shown on FIG. 5 demonstrates that IH4 is a very stable molecule with a transition temperature (Tm) at 75.8° C. (significantly higher than the highest Tm 72.5° C.—which to our knowledge was published for a ScFv (18)). By contrast Tm of p24 is 39° C. indicating a somewhat labile protein; it is interesting to note that a similar Tm value has been published for p24 (19) suggesting that the presence of an extension at the N terminus of our construct (the Polyhistidine tag, a few residues derived from $V_HH$) and the C-terminal HA-tag does not influence p24 thermostability. Finally DSC tracing of the bivalent construct shows essentially a double peak with Tm values of respectively 42.6° C. and 58.5° C.: this does suggest that fusion stabilizes p24 domain and destabilizes IH4 domain. It might be interesting to check if addition of a spacer between the two partners might influence thermostability of the bifunctional molecule. More generally our results suggest that design of bifunctional molecules for autoaggluination assays should take into account thermostability of both partners and thermostability of resulting fusion. In order to increase, if needed, stability of the antigenic part it might be considered to use when possible, peptides instead of full size proteins e.g. either epitope peptides derived from the protein itself or synthetic peptides identified as mimotopes of the antigen target (20 and references cited therein).

Worth noting however, even though IH4 when present as a domain of IH51 seems to be less stable than plain IH4, SPR experiments performed using IH4-p24 as analyte did allow to calculate a $K_D$ of 13.9 nM close to the value measured for the autonomous IH4 (33.7 nM).

Agglutination

Reconstituted blood prepared from HIV positive serum and control was used for the agglutination experiments, a variety of techniques were tested like filtration on gel columns or agglutination in polystyrene plates (21) with consistent results. FIG. 6 shows results acquired using the simplest and quickest glass tile technique. Agglutination is obvious in the drop obtained with 2.5 µg/mL IH51 fusion. A high concentration of reagent does inhibit agglutination a fact which is clearly attributable to competition of soluble IH51 with red cells attached IH51 for binding of antibody present in reconstituted blood since addition of free p24 construct to IH51 inhibits agglutination (see left drop of median row). Agglutination is dependent on the presence of specific antibody in patient plasma since no agglutination is observed whatsoever with control plasma from healthy donors (lower row), agglutination depends on the presence of p24 antigen fused to IH4 since IH4 alone at any concentration does not induce agglutination (one concentration only is shown on median row).

Conclusions

The present invention describes the first VHH isolated after immunization of a camelid against human blood. Indeed, because of the many antigens carried by red cells and their importance to Transfusion Medicine one may surmise that the VHH library might be of interest to isolate useful reagents related to blood typing. Indeed, the presented data focuses on a VHH which recognizes an epitope of glycophorin A that is not related to the blood group determinants carried by this protein. Therefore, this VHH reacts with red cells of all humans with the possible exception of very rare individuals that do not express GPA on their red cells or would express only a recombined version of GPA in which the YPPE sequence is lacking (22-23). It is interesting to note that this very Y52PPE55 sequence has already been identified as the epitope recognized by a murine monoclonal antibody produced after immunization against human red cells [24] proving that this region is rather immunogenic in both mouse and dromedary. A similar observation was made with a VHH against DARC, another red cell membrane protein (13) since the recognized epitope was identical or overlapping to the one often recognized by murine monoclonals against DARC.

Of note, even if a continuous epitope has not been described often for VHH (13, 25) our present and our former (13) results suggest that it should be systematically searched for, keeping in mind that they may offer the opportunity of new tags for identification and purification of recombinant proteins.

Another point worth noting is that affinity of VHH seems to be somewhat modulated by glycans present on its protein target: it has been noted many times that VHH might target cryptic epitopes since their small size allow them to creep more easily to crevices and areas shielded from usual large size antibody (1-3), our results showing that affinity is increased after glycan chains removal suggests however that some steric hindrance may impede partially VHH interaction with its epitope.

The fact that the described VHH has the potential to recognize the red cells of all humans opens some avenues for its application.

Indeed one might imagine fusing IH4 to a drug in order to increase its half life through binding to red cells whose life span in circulation is 120 days. However it is most probable that such an approach would be better performed using a humanized antibody fragment derivative (26) even if VHH are suggested to be poorly immunogenic because of their close relationship to the VH3 and VH4 families of human antibodies (27-28).

Moreover, the VHH of the invention is an excellent substitute to Fab and ScFv used as building blocks of reagents for autologous red cells agglutination assays (7-9). By fusing IH4 to HIV p24 and using reconstituted blood starting from stored frozen plasma of an AIDS patient we demonstrated that we might devise a single component reagent for quick diagnosis of immunization against p24. The inventors pinpoint that VHH had distinct advantages: ease of preparation and yield of our constructs contrast with multistep procedure which were necessary to production of Fab and ScFv derived reagents (7-9). In this regard it should be mentioned that use of SHuffle cells did allow producing several tens of milligrams per Liter of fermentation medium of construct p24-IH4 fusion and of IH4 as soluble and functional protein. SHuffle cells are commercial cells which have been comprehensively described only recently (29). They were developed on a classical BL21 background and were engineered so as to have diminished cytoplasmic reductive pathway and to express a protein disulphide isomerase. Other work, published previously (30) did show that co-expression of both a protein disulphide isomerase and a sulfhydryl oxidase might also allow high yield production of VHH. In our hands every VHH which we produced in SHuffle cells to date was expressed in high yield and mostly in soluble form, in addition we managed to produce proteins from *Plasmodium falciparum* which are notoriously difficult to express because of their numerous disulfide bonds (31), it should not be concealed however that with some other constructs we might get low yield of soluble protein and observe formation of inclusion bodies.

Using IH4 as a fusion partner the inventors demonstrated that it was possible to incorporate it into a reagent applicable in autologous red cells agglutination assays. Indeed presence of antibodies to p24 could be demonstrated within minutes by a very simple procedure. This experiment on one single plasma sample and detecting reactivity to a single antigen (15) is a proof of principle. Although principle of autologous agglutination tests was devised many years ago and its applicability to AIDS diagnosis then demonstrated (7-9) it is not presently established as a reference technique and e.g. none of agglutination assay is recommended by Atlanta Center for Diseases Control for diagnosis of AIDS (33). The reason to the relative lack of recognition is not obvious, relative complexity of preparation of reagents building blocks (Fab and ScFv) may have impeded the development of the technique, use of VHH instead might be an issue. In any case all techniques based solely on detection of immunization do not solve the problem of the serological window during which an infected individual still has no detectable antibody but is nevertheless at risk to transmit the disease through transfusion or sexual intercourse. So called fourth generation (ELISA) tests for HIV infection check for the presence in patient's serum of p24 antigen in addition to the presence of antibodies, since presence of p24 antigen in plasma precedes apparition of antibodies. Detection of virus in plasma through nucleic acid amplification testing is a way to further shorten serological window (34-35). It has to be stressed nevertheless that all these methods are expensive, need adequate logistics, laboratory equipments, expertise which may not be available in resource poor countries; moreover they do not provide immediate results which are beneficial since they may allow quick application of prophylactic and therapeutic measures with a significant impact on public health as detailed elsewhere (36-37).

Obviously the principle of autologous red cell agglutination assay might be applied to other diseases than AIDS such as Sleeping Sickness, a disease which is an increasing threat to inhabitants of the poorest countries of the world (38). Chagas disease (39-40) leishmaniasis (41-42) as well as cysticercosis (43-44) toxocariosis (45) and other human helminth diseases (46) might also be targets for development of autologous red cell agglutination assays. Prerequisite to the development of such reagents is identification of disease specific antigens or mimotopes (20, 40, 45) which then might be fused to IH4, the described VHH. The present invention demonstrates that IH4 is a convenient, versatile, ready to use building block for the design of innovative diagnostic reagents.

REFERENCES

Throughout this application, various references describe the state of the art to which this invention pertains. The disclosures of these references are hereby incorporated by reference into the present disclosure.

1. C. Vincke, C. Gutiérrez, U. Wernery, N. Devoogdt, G. Hassanzadeh-Ghassabeh, S. Muyldermans. Generation of single domain antibody fragments derived from camelids and generation of manifold constructs. Methods Mol Biol. 907 (2012) 145-176.
2. S. Muyldermans, Single domain camel antibodies: current status. J Biotechnol. 74 (2001) 277-302.
3. J. Wesolowski, V. Alzogaray, J. Reyelt, M. Unger, K. Juarez, M. Urrutia, A. Cauerhff, W. Danquah, B. Rissiek, F. Scheuplein, N. Schwarz, S. Adriouch, O. Boyer, M. Seman, A. Licea, D V. Serreze, F A. Goldbaum, F. Haag, F. Koch-Nolte? Single domain antibodies: promising experimental and therapeutic tools in infection and immunity. Med Microbiol Immunol. 198 (2009) 157-174
4. M. Reid, C. Lomas-Francis The Blood Group Antigen FactsBook, 2nd Edition Academic Press? San Diego
5. J P. Cartron, C. Rahuel, MNSs and major glycophorins of human erythrocytes. Transfus Clin Biol. 2 (1995) 251-258.
6. M E. Reid, E. Lisowska, D. Blanchard, Coordinator's report: glycophorin/band 3 and associated antigens. Transfus Clin Biol. 4 (1997) 57-64.
7. B E. Kemp, D B. Rylatt, P G. Bundesen, R R. Doherty, D A. McPhee, D. Stapleton, L E. Cottis, K. Wilson, M A. John, J M Khan, D P. Dinh, S. Miles, C J. Hillyard, Autologous red cell agglutination assay for HIV-1 antibodies: simplified test with whole blood. Science. 241 (1988) 1352-1354.
8. A. Gupta, S. Gupta, V K. Chaudhary, Recombinant fusion proteins for haemagglutination-based rapid detection of antibodies to HIV in whole blood. J Immunol Methods. 256 (2001) 121-140.
9. A. Gupta, V K. Chaudhary, Whole-blood agglutination assay for on-site detection of human immunodeficiency virus infection. J Clin Microbiol. 41 (2003) 2814-2821
10. S. Cochet, G. Volet, J P. Cartron, O. Bertrand, New procedures for glycophorin A purification with high yield and high purity. J Chromatogr B Biomed Sci Appl. 750 (2001) 109-119.
11. E. De Genst, K. Silence, K. Decanniere, K. Conrath, K., R. Loris, J. Kinne, J., S. Muyldermans, L. Wyns, Molecular basis for the preferential cleft recognition by dromedary heavy-chain antibodies. Proc. Natl. Acad. Sci. U.S.A. 103, (2006) 4586-4591.

12. G. Hassanzadeh-Ghassabeh, D. Saerens, S. Muyldermans. Generation of anti-infectome/anti-proteome nanobodies. Methods Mol Biol. 790 (2011) 239-259.
13. D. Smolarek, C. Hattab, G. Hassanzadeh-Ghassabeh, S. Cochet, C. Gutiérrez, AG. de Brevern, R. Udomsangpetch, J. Picot, M. Grodecka, K. Wasniowska, S. Muyldermans, Y. Colin, C. Le Van Kim, M. Czerwinski, O. Bertrand, A recombinant dromedary antibody fragment (VHH or nanobody) directed against human Duffy antigen receptor for chemokines. Cell Mol Life Sci. 67 (2010) 3371-3387
14. H M. Geysen, S J. Rodda, T J. Mason, G. Tribbick, P G Schoofs, Strategies for epitope analysis using peptide synthesis. J Immunol Methods, 102 (1987) 259-274
15. G. Murphy, J V. Parry. Assays for the detection of recent infections with human immunodeficiency virus type 1. Euro Surveill.; 13 (2008) pii=18966.
16. C. Rahuel, J. London, L. d'Auriol, M G. Mattei, C. Tournamille, C. Skrzynia, Y. Lebouc, F. Galibert, J P. Cartron, Characterization of cDNA clones for human glycophorin A. Use for gene localization and for analysis of normal and glycophorin-A-deficient (Finnish type) genomic DNA. Eur J Biochem. 172 (1988) 147-153.
17. M. Duk, M. Ugorski, E. Lisowska, beta-Elimination of O-glycans from glycoproteins transferred to immobilon P membranes: method and some applications. Anal Biochem. 253 (1997) 98-102.
18. R. Mabry, K E. Lewis, M. Moore, P A. McKernan, T R. Bukowski, K. Bontadelli, T. Brender, S. Okada, K. Lum, J. West, J L. Kuijper, D. Ardourel, S. Franke, L. Lockwood, T. Vu, A. Frank, M W. Appleby, A. Wolf, B. Reardon, N B Hamacher, B. Stevens, P. Lewis, K B. Lewis, D G. Gilbertson, M. Lantry, S H. Julien, C. Ostrander, C. Chan, K. Byrnes-Blake, J. Brody, S. Presnell, B. Meengs, S D; Levin, M. Snavely, Engineering of stable bispecific antibodies targeting IL-17A and IL-23. Protein Eng Des Sel. 23 (2010) 115-127
19. R. Misselwitz, G. Hausdorf, K. Welfle, W E. Hohne, H. Welfle. Conformation and stability of recombinant HIV-1 capsid protein p24 (rp24). Biochim Biophys Acta. 1250 (1995) 9-18.
20. L. Van Nieuwenhove, P. Büscher, F. Balharbi, M. Humbert, T. Dieltjens, Y. Guisez, V. Lejon, Identification of mimotopes with diagnostic potential for *Trypanosoma brucei* gambiense variant surface glycoproteins using human antibody fractions. PLoS Negl Trop Dis. 6 (2012) e1682.
21. K A. Downes, I A. Schulman, in: Technical Manual, Roback J, Combs M, Grossman, Ed. 16th edition AABB Bethesda Md. USA 2008 pp. 437-463.
22. C. Rahuel, J. London, A. Vignal, B. Cherif-Zahar, Y. Colin, P. Siebert, M. Fukuda, J P. Cartron, Alteration of the genes for glycophorin A and B in glycophorin-A-deficient individuals. Eur J Biochem. 177 (1988) 605-614.
23. O O. Blumenfeld, C H. Huang. Molecular genetics of glycophorin MNS variants. Transfus Clin Biol. '(1997) 357-365.
24. K. Waśniowska, E. Jaśkiewicz, M. Czerwiński, D. Syper, E. Lisowska, Mapping of peptidic epitopes of glycophorins A (GPA) and C (GPC) with peptides synthesized on plastic pins (Pepscan analysis). Transfus Clin Biol. 4 (1997) 73-75.
25. E. Pardon, J. Steyaert, L. Wyns, Epitope tag for affinity-based applications WIPO Patent Application WO/2011/147890 VIB VZW (Gent) Vrije Universiteit Brussel (Brussel).
26. C. Vincke, R. Loris, D. Saerens, S. Martinez-Rodriguez, S. Muyldermans, K. Conrath, General strategy to humanize a camelid single-domain antibody and identification of a universal humanized nanobody scaffold. J Biol Chem. 284 (2009) 3273-3284.
27. V K. Nguyen, R. Hamers, L. Wyns, S. Muyldermans, Camel heavy-chain antibodies: diverse germline V(H)H and specific mechanisms enlarge the antigen-binding repertoire. EMBO J. 19 (2000) 921-930.
28. N. Deschacht, K. De Groeve, C. Vincke, G. Raes, P. De Baetselier, S. Muyldermans, A novel promiscuous class of camelid single-domain antibody contributes to the antigen-binding repertoire. J Immunol. 184 (2010) 5696-5704.
29. J. Lobstein, C A. Emrich, C. Jeans, M. Faulkner, P. Riggs, M. Berkmen, SHuffle, a novel *Escherichia coli* protein expression strain capable of correctly folding disulfide bonded proteins in its cytoplasm. Microb Cell Fact. 2012; 11:56. doi:10.1186/1475-2859-11-56
30. G. Veggiani, A. de Marco, Improved quantitative and qualitative production of single-domain intrabodies mediated by the co-expression of Erv1p sulfhydryl oxidase. Protein Expr Purif. 79 (2011) 111-114.
31. A. Srivastava, S. Gangnard, S. Dechavanne, F. Amirat, A. Lewit Bentley, G A. Bentley, B. Gamain, Var2CSA minimal CSA binding region is located within the N-terminal region. PLoS One. 6 (2011) e20270.
32. S. Sirivichayakul, P. Phanuphak, S. Tanprasert, S. Thanomchat, C. Uneklabh, T. Phutiprawan, C. Mungklavirat, Y. Panjurai, Evaluation of a 2-minute anti-human immunodeficiency virus (HIV) test using the autologous erythrocyte agglutination technique with populations differing in HIV prevalence. J Clin Microbiol. 31 (1993) 1373-1375.
33. http://www.cdc.gov/hiv/topics/testing/rapid/rt-comparison.htm (Accessed 31 Oct. 2012)
34. M S. Cohen, G M. Shaw, A J. McMichael, B F. Haynes. Acute HIV-1 Infection. N Engl J Med. 364 (2011) 1943-1954.
35. E S. Daar, C D. Pilcher, F M. Hecht, Clinical presentation and diagnosis of primary HIV-1 infection. Curr Opin HIV AIDS. 3 (2008):10-15.
36. D M. Branson Rapid tests for HIV testing AIDS Rev: 2 (2000) 76-83
37. B. Kane. Rapid testing for HIV: why so fast? Ann Intern Med. 131 (1999): 481-3.
38. F. Chappuis, L. Louta, P. Simarro, V. Lejon, P. Büscher, Options for field diagnosis of human african trypanosomiasis. Clin Microbiol Rev. 18 (2005) 133-146.
39. C A. Barfield, R S. Barney, C H. Crudder, J L. Wilmoth, D S. Stevens, S. Mora-Garcia, M J. Yanovsky, B H. Weigl, J. Yanovsky. A highly sensitive rapid diagnostic test for Chagas disease that utilizes a recombinant *Trypanosoma cruzi* antigen. IEEE Trans Biomed Eng. 58 (2011):814-817
40. A W. Ferreira, Z R Belem, E A Lemos, S G Reed, A. Campos-Neto. Enzyme-linked immunosorbent assay for serological diagnosis of Chagas' disease employing a *Trypanosoma cruzi* recombinant antigen that consists of four different peptides. J Clin Microbiol. 39 (2001):4390-4395.
41. F. Chappuis, R. Suman, S. Alonso, J. Menten, M. Boelaert A meta-analysis of the diagnostic performance of the direct agglutination test and rK39 dipstick for visceral leishmaniasis BMJ. 333 (2006): 723-727
42. Y. Goto, R N. Coler, J. Guderian, R. Mohamath, S G. Reed. Cloning, characterization, and serodiagnostic evaluation of *Leishmania infantum* tandem repeat proteins. Infect Immun. 74 (2006):3939-3945.

43. A C. White, Neurocysticercosis: a major cause of neurological disease worldwide. Clin Infect Dis. 24 (1997) 101-113
44. J F. Carod, M. Randrianarison, J. Razafimahefa, R M. Ramahefarisoa, M. Rakotondrazaka, M. Debruyne, M. Dautigny, P. Cazal, M L. Andriantseheno, E R. Charles. Evaluation of the performance of 5 commercialized enzyme immunoassays for the detection of *Taenia solium* antibodies and for the diagnosis of neurocysticercosis. Diagn Microbiol Infect Dis. 72 (2012):85-89.
45. S. Mohamad, N C. Azmi, R. Noordin. Development and evaluation of a sensitive and specific assay for diagnosis of human toxocariasis by use of three recombinant antigens (TES-26, TES-30USM, and TES-120). J Clin Microbiol. 47 (2009):1712-1717.
46. J S. McCarthy, S. Lustigman, G J. Yang, R M. Barakat, H H. Garcia, B. Sripa, A L. Willingham, R K. Prichard, M G. Basáñez. A research agenda for helminth diseases of humans: diagnostics for control and elimination programmes. PLoS Negl Trop Dis. 6 (2012):e1601.

The invention claimed is:

1. An isolated VHH comprising a CDR1 having the sequence set forth as SEQ ID NO: 1, a CDR2 having the sequence set forth as SEQ ID NO:2, and a CDR3 having the sequence set forth as SEQ ID NO:3, wherein said isolated VHH has specificity to glycophorin A.

2. An isolated VHH having an amino acid sequence selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16, wherein said isolated VHH has specificity to glycophorin A.

3. The isolated VHH according to claim 1, wherein said VHH is a humanized VHH.

4. The isolated VHH according to claim 1, wherein said VHH is fused to at least one heterologous polypeptide.

5. The isolated VHH according to claim 4, wherein said heterologous polypeptide comprises:

[a] an infectious antigen,
[b] an antibody, or
[c] a VHH directed against an infectious agent.

6. The isolated VHH according to claim 4, wherein said heterologous polypeptide is a therapeutic polypeptide.

7. A nucleic acid molecule encoding the VHH according to claim 1.

8. A vector comprising the nucleic acid molecule according to claim 7.

9. A host cell comprising the nucleic acid molecule according to claim 7.

10. A method for producing a VHH comprising:
   (i) culturing a transformed host cell according to claim 9 under conditions suitable to allow expression of said VHH; and
   (ii) recovering the expressed VHH.

11. An immunoconjugate comprising the VHH according to claim 1, wherein said VHH is conjugated to at least one therapeutic chemical compound.

12. A method of detecting in vitro the presence of infectious agents in a patient in need thereof, comprising bringing a biological sample of said patient into contact with the isolated VHH of claim 5.

13. A red blood cell agglutination assay for the detection of immunization against infectious agents in a blood sample, comprising:
   (i) bringing the blood sample into contact with the isolated VHH according to claim 5, wherein said VHH is directed against an infectious agent, and
   (ii) concluding that immunization against the infectious agent is present in the patient when the red blood cells are agglutinated, or concluding that immunization is absent or present at a low level in the patient when the red blood cells are not agglutinated.

14. A method of increasing therapeutic polypeptide serum half-life in a patient in need thereof, comprising administering to said patient the isolated VHH according to claim 6.

15. A method of increasing therapeutic chemical compound serum half-life in a patient in need thereof, comprising administering to said patient the isolated VHH according to claim 11.

16. A pharmaceutical composition comprising the isolated VHH according to claim 6.

17. A pharmaceutical composition comprising the isolated VHH according to claim 11.

18. A kit comprising at least one isolated VHH according to claim 4.

19. A kit comprising at least one isolated VHH according to claim 11.

* * * * *

SEQUENCE LISTING

```
<160> NUMBER OF SEQ ID NOS: 17

<210> SEQ ID NO 1
<211> LENGTH: 11
<212> TYPE: PRT
<213> ORGANISM: Artificial
<220> FEATURE:
<223> OTHER INFORMATION: Amino acid sequence of CDR1 from the IH4 VHH

<400> SEQUENCE: 1

Ser Gly Tyr Thr Asp Ser Thr Tyr Cys Val Gly
1               5                   10

<210> SEQ ID NO 2
<211> LENGTH: 17
<212> TYPE: PRT
<213> ORGANISM: Artificial
<220> FEATURE:
<223> OTHER INFORMATION: Amino acid sequence of CDR2 from the IH4 VHH

<400> SEQUENCE: 2

Arg Ile Asn Thr Ile Ser Gly Arg Pro Trp Tyr Ala Asp Ser Val Lys
1               5                   10                  15

Gly

<210> SEQ ID NO 3
<211> LENGTH: 15
<212> TYPE: PRT
<213> ORGANISM: Artificial
<220> FEATURE:
<223> OTHER INFORMATION: Amino acid sequence of CDR3 from the IH4 VHH

<400> SEQUENCE: 3

Thr Thr Ala Asn Ser Arg Gly Phe Cys Ser Gly Gly Tyr Asn Tyr
1               5                   10                  15

<210> SEQ ID NO 4
<211> LENGTH: 11
<212> TYPE: PRT
<213> ORGANISM: Artificial
<220> FEATURE:
<223> OTHER INFORMATION: Amino acid sequence of CDR1 from the 2cPCR51
      VHH

<400> SEQUENCE: 4

Ser Gly Tyr Thr Tyr Ser Thr Tyr Cys Val Gly
1               5                   10

<210> SEQ ID NO 5
<211> LENGTH: 17
<212> TYPE: PRT
<213> ORGANISM: Artificial
<220> FEATURE:
<223> OTHER INFORMATION: Amino acid sequence of CDR2 from the 2cPCR51
      VHH
```

```
<400> SEQUENCE: 5

Pro Ile Asn Thr Val Gly Asp Thr Pro Trp Tyr Ala Asp Ser Val Lys
 1               5                  10                  15

Gly

<210> SEQ ID NO 6
<211> LENGTH: 15
<212> TYPE: PRT
<213> ORGANISM: Artificial
<220> FEATURE:
<223> OTHER INFORMATION: Amino acid sequence of CDR3 from the rcPCR18
      VHH

<400> SEQUENCE: 6

Thr Thr Ala Asn Ser Arg Gly Leu Cys Ser Gly Gly Tyr Asn Tyr
 1               5                  10                  15

<210> SEQ ID NO 7
<211> LENGTH: 122
<212> TYPE: PRT
<213> ORGANISM: Artificial
<220> FEATURE:
<223> OTHER INFORMATION: Amino acid sequence from the IH4 VHH

<400> SEQUENCE: 7

Gln Val Gln Leu Gln Glu Ser Gly Gly Gly Ser Val Gln Ala Gly Gly
 1               5                  10                  15

Ser Leu Arg Leu Ser Cys Val Ala Ser Gly Tyr Thr Asp Ser Thr Tyr
             20                  25                  30

Cys Val Gly Trp Phe Arg Gln Ala Pro Gly Lys Glu Arg Glu Gly Val
         35                  40                  45

Ala Arg Ile Asn Thr Ile Ser Gly Arg Pro Trp Tyr Ala Asp Ser Val
     50                  55                  60

Lys Gly Arg Phe Thr Ile Ser Gln Asp Asn Ser Lys Asn Thr Val Phe
 65                  70                  75                  80

Leu Gln Met Asn Ser Leu Lys Pro Glu Asp Thr Ala Ile Tyr Tyr Cys
                 85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
        115                 120

<210> SEQ ID NO 8
<211> LENGTH: 122
<212> TYPE: PRT
<213> ORGANISM: Artificial
<220> FEATURE:
<223> OTHER INFORMATION: Amino acid sequence from the rcPCR25 VHH

<400> SEQUENCE: 8

Gln Val Gln Leu Gln Glu Ser Gly Gly Gly Ser Val Gln Ala Gly Gly
 1               5                  10                  15

Ser Leu Arg Leu Ser Cys Val Ala Ser Gly Tyr Thr Asp Ser Thr Tyr
             20                  25                  30

Cys Val Gly Trp Phe Arg Gln Ala Pro Gly Lys Glu Arg Glu Gly Val
         35                  40                  45

Ala Arg Ile Asn Thr Ile Ser Gly Arg Pro Trp Tyr Ala Asp Ser Val
     50                  55                  60

Lys Gly Arg Phe Thr Ile Ser Gln Asp Asn Ser Lys Asn Ala Val Phe
 65                  70                  75                  80
```

```
Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
        115                 120

<210> SEQ ID NO 9
<211> LENGTH: 122
<212> TYPE: PRT
<213> ORGANISM: Artificial
<220> FEATURE:
<223> OTHER INFORMATION: Amino acid sequence from the 2cPCR21 VHH

<400> SEQUENCE: 9

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
            35                  40                  45

Ala Arg Ile Asn Thr Ile Ser Gly Arg Pro Trp Tyr Ala Asp Ser Val
        50                  55                  60

Lys Gly Arg Phe Thr Ile Ser Gln Asp Asn Ser Lys Asn Thr Val Phe
65                  70                  75                  80

Leu Gln Met Asn Ser Leu Lys Pro Glu Asp Thr Ala Ile Tyr His Cys
                85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
        115                 120

<210> SEQ ID NO 10
<211> LENGTH: 122
<212> TYPE: PRT
<213> ORGANISM: Artificial
<220> FEATURE:
<223> OTHER INFORMATION: Amino acid sequence from the 2cPCR56 VHH

<400> SEQUENCE: 10

Gln Val Gln Leu Gln Glu Ser Gly Gly Gly Val Val Gln Ala Gly Gly
1               5                   10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
            35                  40                  45

Ala Arg Ile Asn Thr Ile Ser Gly Arg Pro Trp Tyr Ala Asp Ser Val
        50                  55                  60

Lys Gly Arg Phe Thr Ile Ser Gln Asp Asn Ser Lys Asn Thr Val Phe
65                  70                  75                  80

Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
        115                 120
```

```
<210> SEQ ID NO 11
<211> LENGTH: 122
<212> TYPE: PRT
<213> ORGANISM: Artificial
<220> FEATURE:
<223> OTHER INFORMATION: Amino acid sequence from the rcPCR07 VHH

<400> SEQUENCE: 11

Gln Val Gln Leu Gln Glu Ser Gly Gly Gly Val Val Gln Pro Gly Gly
1               5                   10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
        35                  40                  45

Ala Arg Ile Asn Thr Ile Ser Gly Arg Pro Trp Tyr Ala Asp Ser Val
    50                  55                  60

Lys Gly Arg Phe Thr Ile Ser Gln Asp Asn Ser Lys Asn Thr Val Phe
65                  70                  75                  80

Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
        115                 120

<210> SEQ ID NO 12
<211> LENGTH: 122
<212> TYPE: PRT
<213> ORGANISM: Artificial
<220> FEATURE:
<223> OTHER INFORMATION: Amino acid sequence from the 2cPCR11 VHH

<400> SEQUENCE: 12

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
        35                  40                  45

Ala Arg Ile Asn Thr Ile Ser Gly Arg Pro Trp Tyr Ala Asp Ser Val
    50                  55                  60

Lys Gly Arg Phe Thr Ile Ser Gln Asp Asn Ser Lys Ser Thr Val Phe
65                  70                  75                  80

Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
        115                 120

<210> SEQ ID NO 13
<211> LENGTH: 122
<212> TYPE: PRT
<213> ORGANISM: Artificial
<220> FEATURE:
<223> OTHER INFORMATION: Amino acid sequence from the rcPCR26 VHH

<400> SEQUENCE: 13

Gln Val Gln Leu Gln Glu Ser Gly Gly Gly Ser Val Gln Ala Gly Gly
1               5                   10                  15
```

```
Ser Leu Arg Leu Ser Cys Ala Ala Ser Gly Tyr Thr Asp Ser Thr Tyr
            20                  25                  30

Cys Val Gly Trp Phe Arg Gln Ala Pro Gly Lys Glu Arg Glu Gly Val
            35                  40                  45

Ala Arg Ile Asn Thr Ile Ser Gly Arg Pro Trp Tyr Ala Asp Ser Val
            50                  55                  60

Lys Gly Arg Phe Thr Ile Ser Gln Asp Asn Ser Lys Asn Thr Val Phe
65                  70                  75                  80

Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
            115                 120

<210> SEQ ID NO 14
<211> LENGTH: 122
<212> TYPE: PRT
<213> ORGANISM: Artificial
<220> FEATURE:
<223> OTHER INFORMATION: Amino acid sequence from the 2cPCR27 VHH

<400> SEQUENCE: 14

Gln Val Gln Leu Gln Glu Ser Gly Gly Gly Ser Val Gln Ala Gly Gly
1               5                   10                  15

Ser Leu Arg Leu Ser Cys Leu Ala Ser Gly Tyr Thr Asp Ser Thr Tyr
            20                  25                  30

Cys Val Gly Trp Phe Arg Gln Ala Pro Gly Lys Glu Arg Glu Gly Val
            35                  40                  45

Ala Arg Ile Asn Thr Ile Ser Gly Arg Pro Trp Tyr Ala Asp Ser Val
            50                  55                  60

Lys Gly Arg Phe Thr Ile Ser Gln Asp Asn Ser Lys Asn Thr Val Phe
65                  70                  75                  80

Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
            115                 120

<210> SEQ ID NO 15
<211> LENGTH: 122
<212> TYPE: PRT
<213> ORGANISM: Artificial
<220> FEATURE:
<223> OTHER INFORMATION: Amino acid sequence from the rcPCR18 VHH

<400> SEQUENCE: 15

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
            35                  40                  45

Ala Arg Ile Asn Thr Ile Ser Gly Arg Pro Trp Tyr Ala Asp Ser Val
            50                  55                  60

Lys Gly Arg Phe Thr Ile Ser Gln Asp Asn Ser Lys Asn Thr Val Phe
```

```
                65                  70                  75                  80
Leu Gln Met Asn Ser Leu Lys Pro Glu Asp Thr Ala Ile Tyr Tyr Cys
                    85                  90                  95

Thr Leu Thr Thr Ala Asn Ser Arg Gly Leu Cys Ser Gly Gly Tyr Asn
                    100                 105                 110

Tyr Lys Gly Gln Gly Gln Val Thr Val Ser
            115                 120

<210> SEQ ID NO 16
<211> LENGTH: 122
<212> TYPE: PRT
<213> ORGANISM: Artificial
<220> FEATURE:
<223> OTHER INFORMATION: Amino acid sequence from the 2cPCR51 VHH

<400> SEQUENCE: 16

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Tyr Ser Thr Tyr
                20                  25                  30

Cys Val Gly Trp Ile Arg Gln Ala Pro Gly Lys Glu Arg Glu Gly Val
            35                  40                  45

Ala Pro Ile Asn Thr Val Gly Asp Thr Pro Trp Tyr Ala Asp Ser Val
        50                  55                  60

Lys Gly Arg Phe Thr Ile Ser Gln Asp Asn Ser Lys Asn Thr Val Phe
65                  70                  75                  80

Leu Gln Met Asn Ser Leu Lys Pro Glu Asp Thr Ala Ile Tyr Tyr Cys
                    85                  90                  95

Thr Leu Thr Thr Ala Asn Ser Arg Gly Phe Cys Ser Gly Gly Tyr Asn
                    100                 105                 110

Tyr Lys Gly Gln Gly Gln Val Thr Val Ser
            115                 120

<210> SEQ ID NO 17
<211> LENGTH: 4
<212> TYPE: PRT
<213> ORGANISM: Homo sapiens

<400> SEQUENCE: 17

Tyr Pro Pro Glu
1
```